(12) United States Patent
Lee et al.

(10) Patent No.: US 8,586,198 B2
(45) Date of Patent: Nov. 19, 2013

(54) DENDRITIC MOLECULE CONTAINING METAL PHTHALOCYANINE, METHOD OF PREPARING THE SAME AND ORGANIC LIGHT EMITTING DIODE COMPRISING THE DENDRITIC MOLECULE

(75) Inventors: Tae-Woo Lee, Yongin-si (KR); Jong-Jin Park, Yongin-si (KR); Lyong-Sun Pu, Yongin-si (KR); Masa-Aki Kakimoto, Tokyo (JP)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 1251 days.

(21) Appl. No.: 11/987,274

(22) Filed: Nov. 28, 2007

(65) Prior Publication Data
US 2008/0199732 A1   Aug. 21, 2008

(30) Foreign Application Priority Data
Dec. 11, 2006 (KR) .......................... 10-2006-0125859

(51) Int. Cl.
*H01L 51/54* (2006.01)

(52) U.S. Cl.
USPC ........... 428/690; 428/917; 313/504; 313/505; 313/506; 257/40; 257/E51.05; 257/E51.026; 257/E51.032; 540/130; 540/135; 540/139; 540/140

(58) Field of Classification Search
USPC ................. 428/690, 917; 313/504, 505, 506; 548/440; 540/130, 135, 139, 140; 257/40, E51.05, E51.026, E51.032
See application file for complete search history.

(56) References Cited

U.S. PATENT DOCUMENTS

| 4,120,865 | A  | * | 10/1978 | Ward ............................ 540/129 |
| 6,566,807 | B1 | * | 5/2003  | Fujita et al. .................... 313/506 |
| 2003/0091860 | A1 | * | 5/2003 | Oshiyama et al. ............ 428/690 |

FOREIGN PATENT DOCUMENTS

| JP | 08-302224 A  | 11/1996 |
| JP | 10-036830 A  | 2/1998  |
| KR | 100682866 B1 | 2/2007  |

OTHER PUBLICATIONS

Wohrle et. al., Polymeric Phthalocyanines . . . , 1988, Makromol. Chem., vol. 189, pp. 1167-1187.*
Korean Registration Determination Certificate issued on Jun. 27, 2013 by KIPO corresponding to Korean Patent Application No. 10-2006-0125859 and Request for Entry of the Accompanying Office Action attached herewith.
Nail B. MaKeown, "Phthalocyanine-containing polymers", J. Mater. Chem., 2000, 10, 1979-1995.
Korean Office Action issued on Apr. 23, 2013 by KIPO in connection with Korean Patent Application No. 10-2006-0125859 and Request for Entry of the Accompanying Office Action attached herewith.

* cited by examiner

*Primary Examiner* — D. Lawrence Tarazano
*Assistant Examiner* — Gregory Clark
(74) *Attorney, Agent, or Firm* — Robert E. Bushnell, Esq.

(57) ABSTRACT

A dendritic molecule represented by Formula 3:

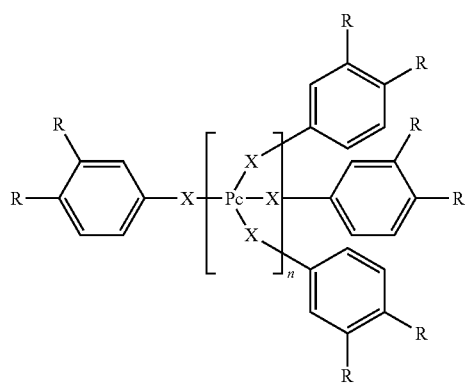
(1)

where Pc is metal phthalocyanine represented by Formula 2:

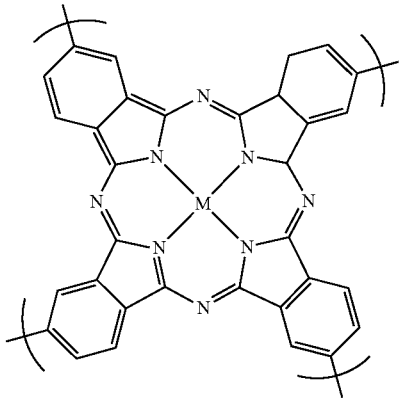
(2)

where M is a core metal of the dendritic molecule; n is an integer in the range of 1 to 50; each of the Xs is a bivalent linking group independently selected from the group consisting of O, S, $CH_2$, CO, $SO_2$ and NHCO; and each of the Rs is independently selected from the group consisting of CN, COOH, $SO_3H$ and $PO_3H$. The dendritic molecule containing metal phthalocyanine is dissolved in an organic solvent, and thus can be used to easily form a hole injection layer or a hole transport layer using solution deposition. The hole injection layer comprising the dendritic molecule containing metal phthalocyanine has good adhesion to an electrode and improved hole injection ability. The organic light emitting diode including the hole injection layer exhibits high luminance and emitting efficiency.

19 Claims, 3 Drawing Sheets

DENDRITIC MOLECULE CONTAINING METAL PHTHALOCYANINE, METHOD OF PREPARING THE SAME AND ORGANIC LIGHT EMITTING DIODE COMPRISING THE DENDRITIC MOLECULE

CROSS-REFERENCE TO RELATED PATENT APPLICATION AND CLAIM OF PRIORITY

This application claims the benefit of Korean Patent Application No. 10-2006-0125859, filed on Dec. 11, 2006, in the Korean Intellectual Property Office, the disclosure of which is incorporated herein in its entirety by reference.

BACKGROUND OF THE INVENTION

1. Field of the Invention

The present invention relates to a dendritic molecule containing metal phthalocyanine and an organic light emitting diode comprising the same, and more particularly, to a dendritic molecule that can be used to form a hole injection layer and an electron injection layer by a solution process that uses an organic solvent, and can improve luminance and emitting efficiency of an organic light emitting diode and an organic light emitting diode including the same.

2. Description of the Related Art

Organic light emitting diodes are self-emissive displays using a phenomenon that when voltage is applied to a fluorescent or phosphorous organic film, electrons and holes are combined in the organic film for light to be emitted. Since organic light emitting diodes are small-sized, have simplified components and simple manufacturing processes, can implement high image quality and high color purity, have low power consumption, can perfectly implement live images and the like, extensive research on organic light emitting diodes has been actively conducted.

Organic light emitting diodes can include several layers such as hole-related layers, for example, a hole injection layer and a hole transport layer and electron-related layers, for example, an electron transport layer and an electron injection layer, in addition to an organic emissive layer, between an anode or a cathode. The hole-related layers and the electron-related layers adjust injection or mobility of electrons or holes from the cathode and the anode. In addition, the anode may comprise an inorganic material such as ITO or IZO, and thus may have a high surface hardness. Surface toughness of the anode may be reduced by introducing a hole injection layer to the organic light emitting diode before a hole transport layer or an emissive layer is formed. In some cases, by introducing a functional group that can improve chemical binding with or absorption to an anode into a material used to form a hole injection layer, adhesion at an interface between an anode (inorganic) and an organic layer (organic) can be improved. In addition, when a difference in ionization potential between the work function of the anode comprising ITO and IZO and an organic layer such as a hole transport layer or an emissive layer that is formed on the anode is so large that hole injection is difficult, a hole injection layer can be introduced in order to easily inject holes. The hole injection layer that is formed on the anode can be also referred to as a buffer layer.

Materials that can form the hole injection layer by a solution process are preferable since the solution process costs low. Of these materials, a polymer material such as PEDOT/PSS in which poly(ethylenedioxy)thiophene (PEDOT) is doped with polystyrene sulfonate (PSS) is commercially available. The material (PEDOT/PSS) is commercially available as a product name of Baytron-P from Bayer AG, and widely used as a material used to form a hole injection layer. A deposition process of a hole injection layer uses an aqueous solution, thereby not being able to be performed within a glove box. Therefore, after the hole injection layer is formed on an electrode outside the glove box, a heat-treatment process, in the glove box, that uses a hot plate or a vacuum oven is required for removing moisture remaining. In addition, a subsequent organic layer is also formed inside the glove box in order to prevent the infiltration of moisture and oxygen.

PSS in PEDOT/PSS is degraded by a reaction with electrons to produce a material such as sulfate or the like. As a result, the material is diffused into an adjacent organic film, for example, an emissive layer. However, the diffusion of the material from a hole injection layer into the emissive layer causes exciton quenching, resulting in reduction in efficiency and lifetime of an organic light emitting diode.

To address such problems, there is a need to develop a material that can be used to form a hole injection layer by a solution process that uses an organic solvent, and has good adhesion to ITO and IZO.

SUMMARY OF THE INVENTION

The present invention provides a dendritic molecule.

The present invention also provides a method of preparing the dendritic molecule.

The present invention also provides an organic light emitting diode comprising the dendritic molecule.

According to an aspect of the present invention, there is provided a dendritic molecule obtained from a reaction of a compound represented by Formula 3 and a metal or a metal compound, the dendritic molecule including metal phthalocyanine represented by Formula 2:

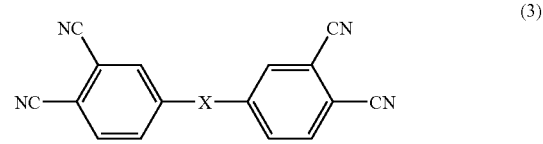

where X is a bivalent linking group selected from the group consisting of O, S, $CH_2$, CO, $SO_2$ and NHCO;

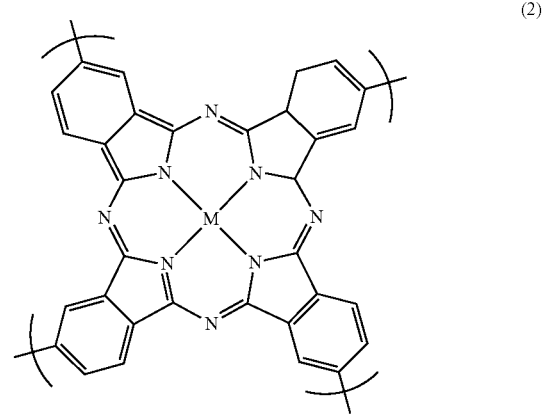

where M is a core metal of the dendritic molecule.

The metal or the metal compound may include a metal element selected from the group consisting of Cu, Co, Ni, Ti, Fe, Ru and Zn.

According to an aspect of the present invention, there is provided a dendritic molecule represented by Formula 1:

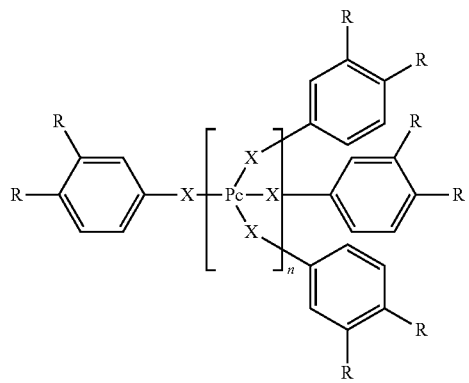

(1)

where Pc is metal phthalocyanine represented by Formula 2:

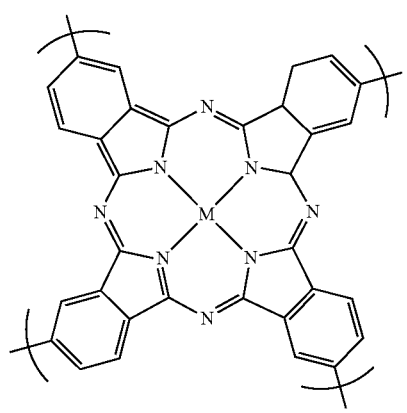

(2)

where M is a core metal of the dendritic molecule; n is an integer in the range of 1 to 50; each of the Xs is a bivalent linking group independently selected from the group consisting of O, S, $CH_2$, CO, $SO_2$ and NHCO; and each of the Rs is independently selected from the group consisting of CN, COOH, $SO_3H$ and $PO_3H$.

The dendritic molecule may have a molecular weight of 1,000 to 100,000.

According to an aspect of the present invention, there is provided a method of preparing a dendritic molecule, comprising: reacting a compound represented by Formula 3 with a metal or a metal compound; and optionally replacing the CN groups with a group R which is selected from the group consisting of COOH, $SO_3H$ and $PO_3H$:

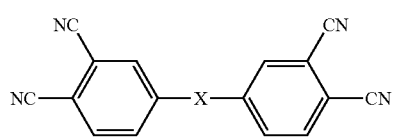

(3)

where X is a bivalent linking group selected from the group consisting of O, S, $CH_2$, CO, $SO_2$ and NHCO.

The compound represented by Formula 3 may be reacted with the metal comprised of a metal powder, and the molar ratio of the compound of Formula 3 and the metal powder is 4:1 to 3:1. Alternatively, the compound represented by Formula 3 may be reacted with the metal compound comprised of a metal halide, and the molar ratio of the compound of Formula 3 and the metal halide is 2:1 to 3:2.

The reaction of the compound represented by Formula 3 with the metal or the metal compound can be performed at a temperature in the range of 100 to 200° C. for 1 minute to 30 hours.

The method may further include hydrolyzing the product obtained from the reaction of the compound represented by Formula 3 with the metal or the metal compound.

According to an aspect of the present invention, there is provided an organic light emitting diode, comprising: a first electrode; a second electrode facing the first electrode; and an organic layer interposed between the first electrode and the second electrode, the organic layer comprising a layer comprised of a dendritic molecule represented by Formula 1:

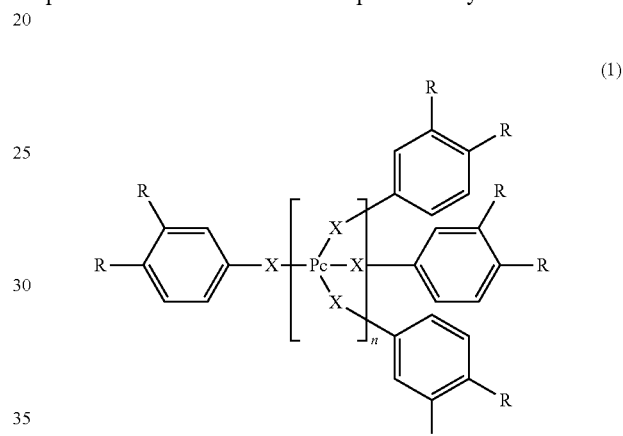

(1)

where Pc is metal phthalocyanine represented by Formula 2:

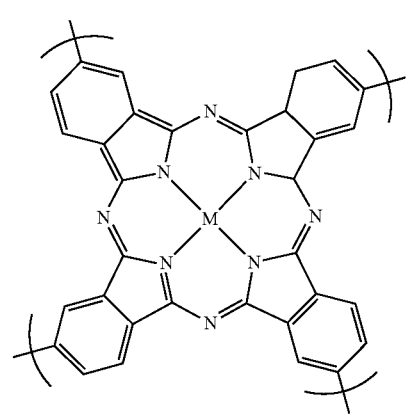

(2)

where M is a core metal of the dendritic molecule; n is an integer in the range of 1 to 50; each of the Xs is a bivalent linking group independently selected from the group consisting of O, S, $CH_2$, CO, $SO_2$ and NHCO; and each of the Rs is independently selected from the group consisting of CN, COOH, $SO_3H$ and $PO_3H$.

The layer comprised of the dendritic molecule represented by Formula 1 may be a buffer layer, a hole injection layer or a hole transport layer.

The above information disclosed in this Background section is only for enhancement of understanding of the background of the invention and therefore it may contain information that does not form the prior art that is already known in this country to a person of ordinary skill in the art.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Hereinafter, the present invention will be described more fully with reference to the accompanying drawings, in which exemplary embodiments of the invention are shown.

In the present specification, when only one layer that makes it easy for holes to be injected and transported is formed between an anode and an emissive layer, the layer can be referred to as either a hole injection layer or a hole transport layer as conventionally referred, or as a buffer layer.

The term "dendritic molecule" includes a hyperbranched polymer and dendrimer. The hyperbranched polymer refers to a multiple-branched polymer. The hyperbranched polymer is generally synthesized by a self-condensation reaction of a compound having two types of reactable sites in one molecule. A dendrimer refers to repeatedly branched species in which branch-type unit structures repeatedly extend in a direction away from the core metal. When a unit structure that is uniformly repeated is added to the dendrimer, it is said that the generation of the dendrimer increases.

According to an embodiment of the present invention, there is provided a dendritic molecule that can be represented by Formula 1:

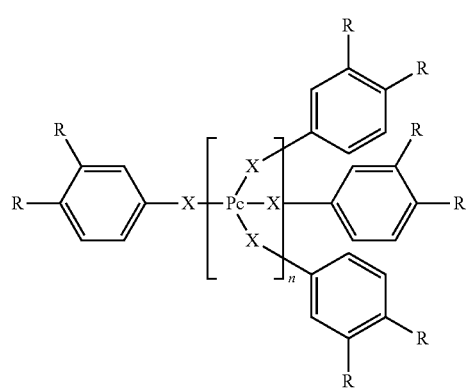

(1)

where Pc is metal phthalocyanine represented by Formula 2:

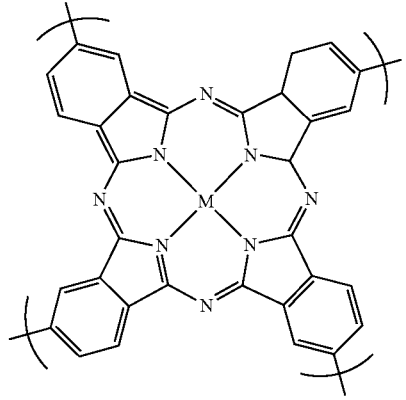

(2)

where n is an integer in the range of 1 to 50;

each of Xs is a bivalent coupler independently selected from the group consisting of $O$, $S$, $CH_2$, $CO$, $SO_2$ and $NHCO$; and each of Rs is a group independently selected from the group consisting of $CN$, $COOH$, $SO_3H$ and $PO_3H$, and is the same as or different from each other.

In Formula 1,

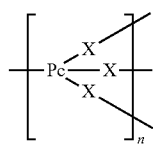

includes repeatedly branched structures, and the generation numbers of the branches may be the same or different from each other.

Figure 1:
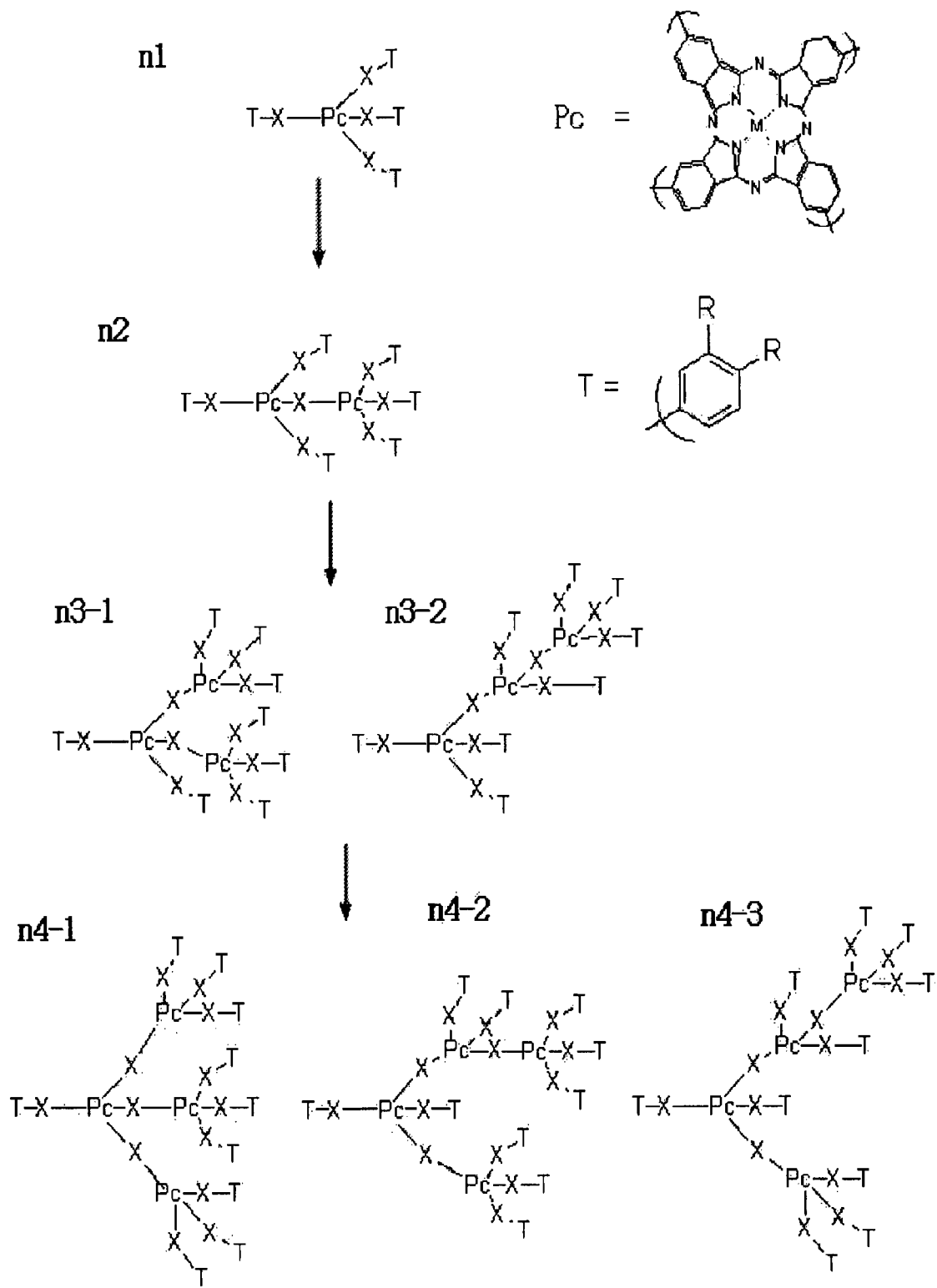
FIG. 1 is a schematic diagram illustrating a method of forming a dendritic molecule or a hyperbranched polymer according to an embodiment of the present invention.

FIG. 1 is a schematic diagram illustrating a method of forming a dendritic molecule containing metal phthalocyanine according to an embodiment of the present invention. In the structure of each dendritic molecule, Pc refers to a phthalocyanine group containing a core metal M as illustrated on the right upper side of FIG. 1. T is a terminal group of the dendritic molecule, and refers to an aromatic ring including two groups as illustrated on the right side of FIG. 1. n is the same as represented in Formula 1. In Formula 1, when n is 1, the dendritic molecule can be represented as a structure of n1 illustrated in FIG. 1. In n1, the dendritic molecule includes one metal phthalocyanine in a central portion, and four terminal groups T are bound to the metal phthalocyanine by a bivalent linking group X. In Formula 1, when n is 3, the dendritic molecule is represented by n3-1 or n3-2 of FIG. 1. Considering only metal phthalocyanine PCS, 3n-1 is of branched structure, while 3n-2 is of linear structure. When n is 4 in Formula 1, the dendritic molecule can be represented by n4-1, n4-2 or n4-3 of FIG. 1.

In the dendritic molecule represented by Formula 1 according to the embodiment of the present invention, the bivalent linking group X is not particularly limited and can be any bivalent linking group that can bind two aromatic rings that are adjacent to each other. However, in order for an undesired side reaction not to occur in a process of synthesizing metal phthalocyanine, the bivalent linking group X may be preferably selected from the group consisting of O, S, CH$_2$, CO, SO$_2$ or NHCO, and more preferably, O and S in terms of stability of a final product.

In the dendritic molecule represented by Formula 1 according to the embodiment of the present invention, a group R that substitutes for a hydrogen of a peripheral aromatic ring of the dendritic molecule may be preferably selected from the group consisting of CN, COOH, SO$_3$H or PO$_3$H to enhance efficiency of an organic light emitting diode by improving adhesiveness to an electrode. More preferably, the group R may be one selected from COOH, SO$_3$H and PO$_3$H, and particularly, COOH.

A core metal M of metal phthalocyanine that is included in the dendritic molecule according to the embodiment of the present invention is not particularly limited, and can be any metal that can form a phthalocyanine-metal complex with an organic compound. However, the core metal M may be Cu, Co, Ni, Ti, Fe, Ru, or Zn, and more preferably, Cu in terms of conductivity and ionized potential of a material, efficiency of an organic light emitting diode and the like.

The dendritic molecule containing metal phthalocyanine according to the embodiment of the present invention can be synthesized using a compound represented by Formula 3:

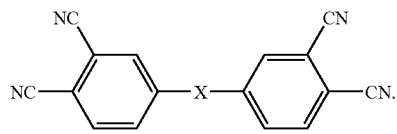
(3)

The compound represented by Formula 3 can be any compound in which 2 dicyano phenyl groups are bound to each other by a bivalent linking group, wherein the dicyano phenyl group has two cyano groups that are adjacent to each other, but is not particularly limited. Examples of the compound represented by Formula 3 include the following compounds represented by Formulae 3A to 3E:

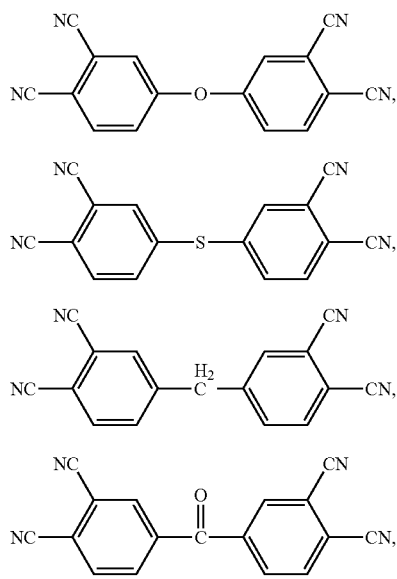

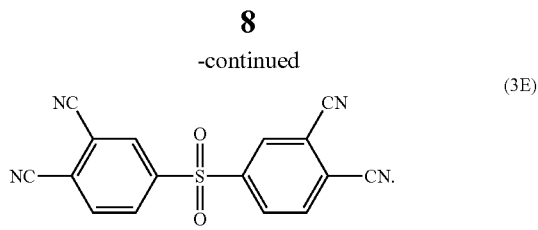

In an embodiment of the present invention, examples of the smallest dendritic molecule include the following compounds represented by Formulae 4A through 4H, but are not limited thereto:

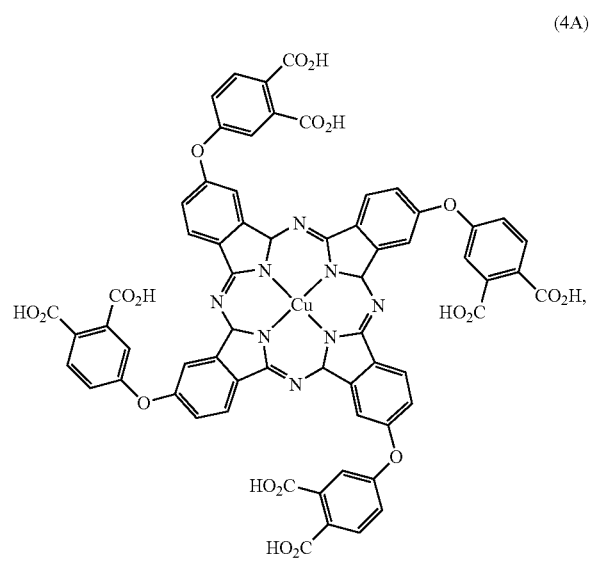

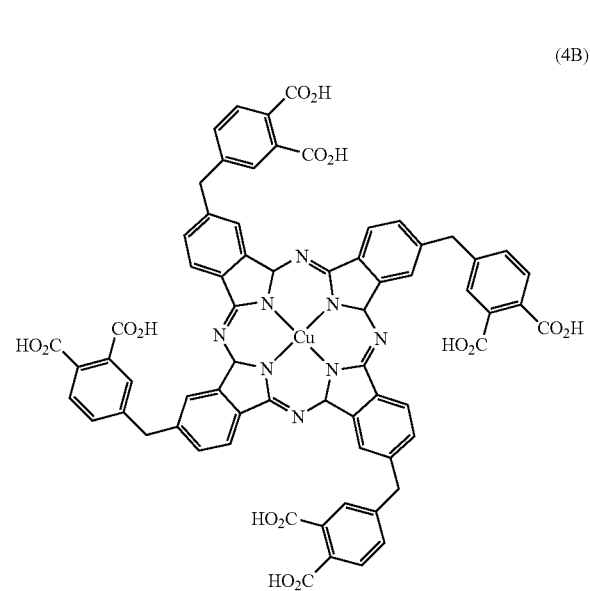

-continued
(4C)
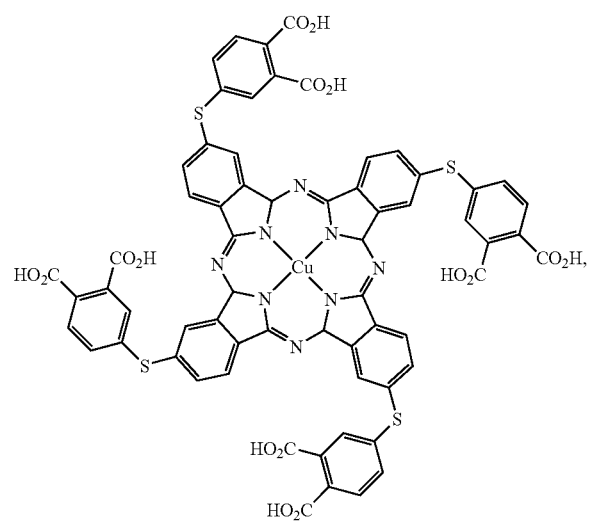
(4D)
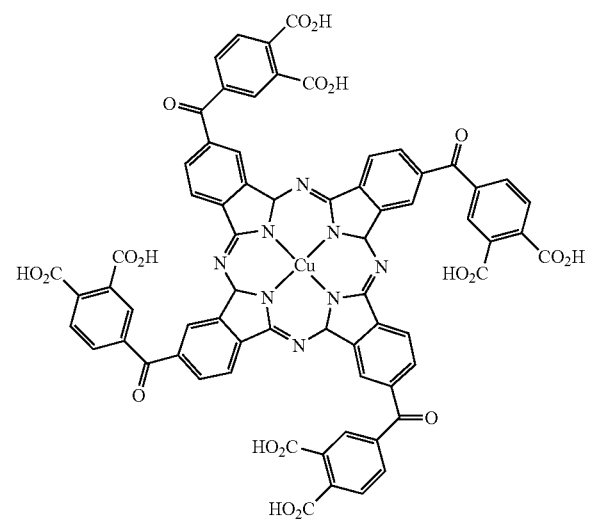
(4E)
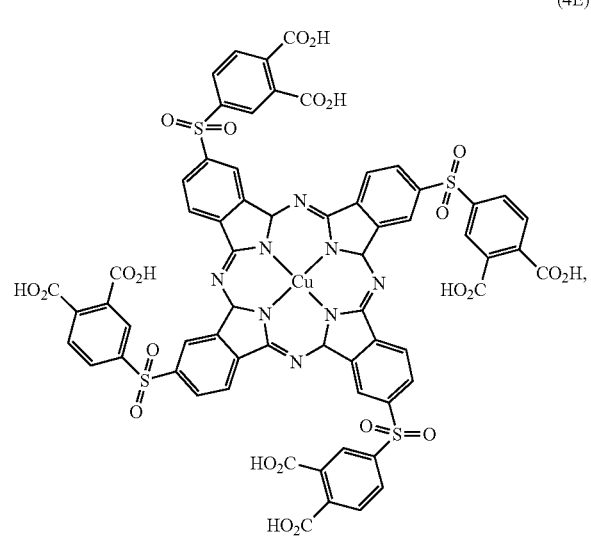
-continued
(4F)
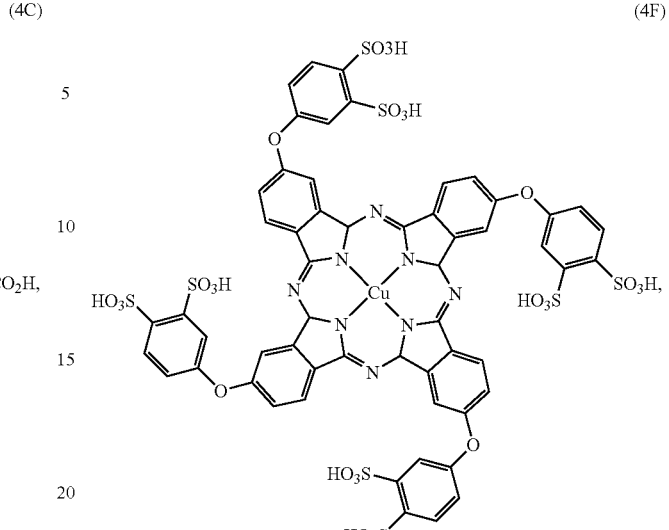
(4G)
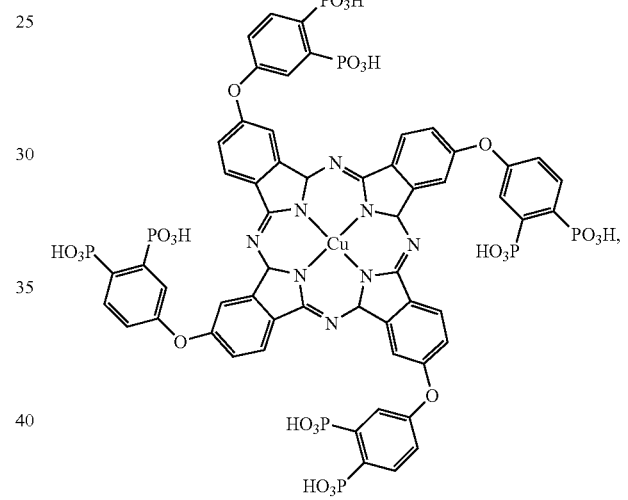
(4H)
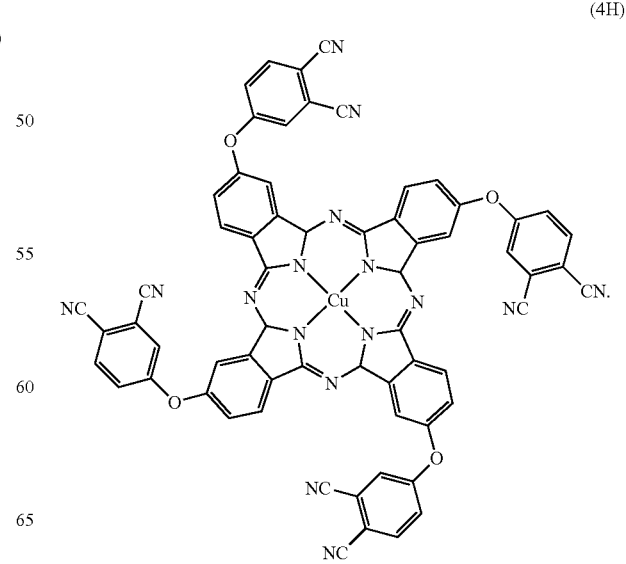

Although the compounds illustrated above contain Cu as a core metal, they may also contain Co, Ni, Ti, Fe, Ru or Zn in place of Cu as a core metal of a phthalocyanine group.

According to an embodiment of the present invention, the compound represented by Formula 1 can be a compound represented by Formula 5:

Formula 1 are combined to one another to form a unit structure of metal phthalocyanine, more compounds represented by Formula 1 are further combined by successive chemical boding to form a huge branch structure, and the CN groups are replaced with COOH groups. When represented by Formula 1, the dendritic molecule of Formula 5 has n of 3 and the bivalent linking group R of O and the aromatic group R of COOH.

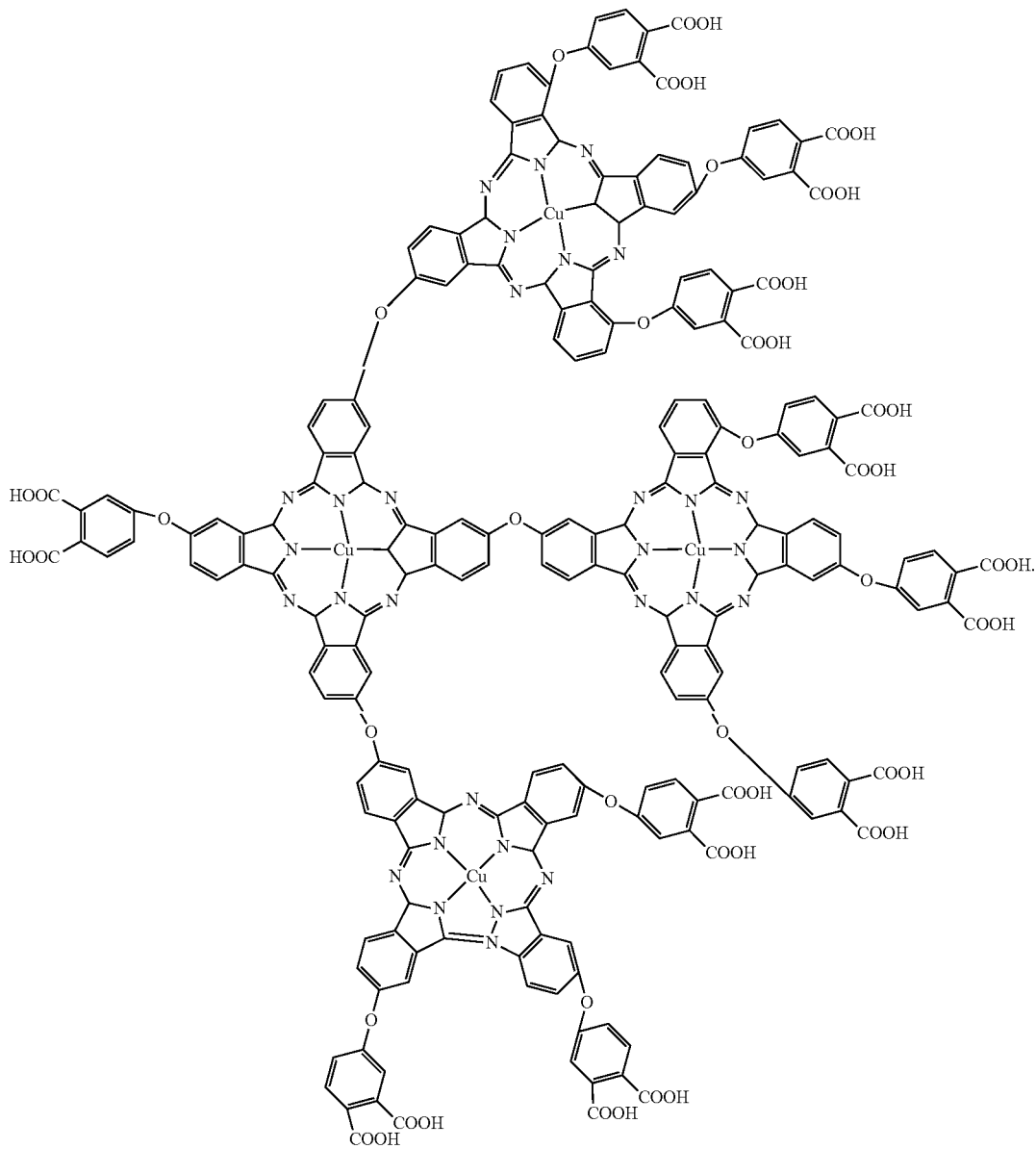

(5)

In Formula 5, the dendritic molecule containing Cu-phthalocyanine according to an embodiment of the present invention is formed in such a way that 4 compounds represented by When the dendritic molecule represented by Formula 5 further includes one Cu-phthalocyanine unit structure, a compound represented by Formula 6 below can be formed:

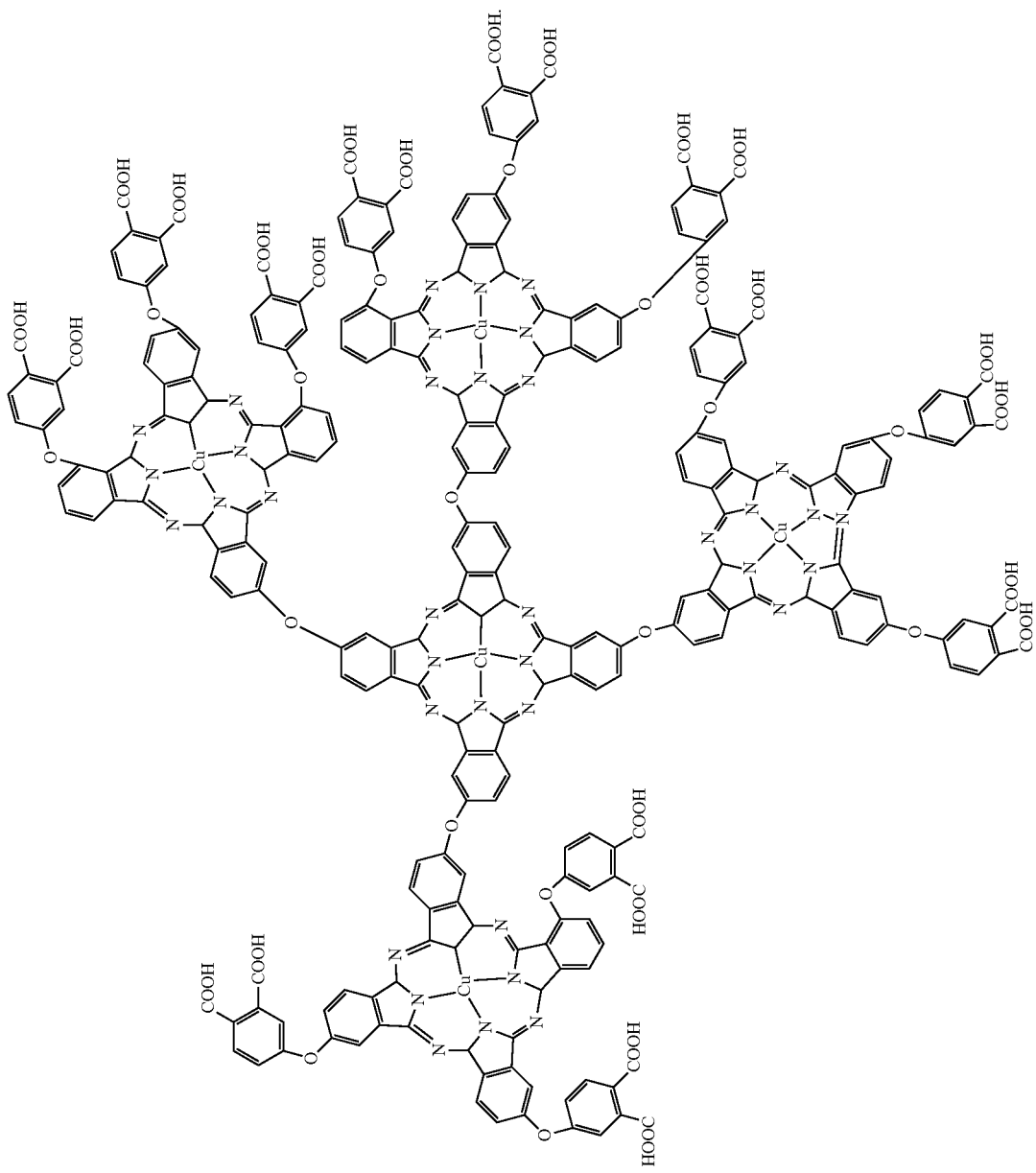
(6)

According to an embodiment of the present invention, there is provided a method of forming a dendritic molecule containing metal phthalocyanine.

In the method of forming a dendritic molecule containing metal phthalocyanine according to the embodiment of the present invention, first, the compound represented by Formula 3 is reacted with a metal ion such as copper or the like to form metal phthalocyanine. Then, the formed metal phthalocyanine is further reacted with the compound represented by Formula 3 to form a dendritic oligomer or a dendritic polymer.

The compound represented by Formula 3 is dissolved in a solvent with a metal including Cu or the like or a metal compound. Here, the metal can be a metal powder type, and the metal compound can be a metal halide type. Examples of the metal halide include copper chloride, copper bromide, copper iodides, cobalt dichloride, nickel, titanium, chloride, ferric chloride, ruthenium chloride, zinc chloride and the like, but are not limited thereto.

When a metal halide is used, the molar ratio of the compound represented by Formula 3 and the metal halide may be 2:1 to 3:2. When a metal powder is used, the molar ratio of the compound represented by Formula 3 and the metal power may be 4:1 to 3:1. When the amount of the metal powder is less than this range, metal phthalocyanine is not substantially formed and thus it is difficult to form copper phthalocyanine hyperbranched polymer or copper phthalocyanine dendrimer. When the amount of the metal powder is greater than this range, solubility of the product with respect to a solvent is reduced, and thus the reaction is not smoothly performed. The solvent used in the reaction can be acetone, tetrahydrofuran, dimethyl acetamide, N-methyl-2-pyrolidone or the like.

The solution prepared by dissolving the compound represented by Formula 3 and a metal or a metal compound in the solvent is reacted at about 160° C. for one minute to 30 hours. The molecular weight of the dendritic molecule containing metal phthalocyanine used in the present invention can be adjusted by controlling polymerization reaction conditions thereof. When the polymerization reaction is performed for less than one minute, it is difficult to form a desired metal phthalocyanine polymer. On the other hand, when the polymerization reaction is performed for greater than 30 hours, the molecular weight of the dendritic molecule containing metal phthalocyanine can be so large that solubility thereof is reduced so that manufacturing an organic light emitting diode using a solution process is difficult. In general, the molecular weight of the dendritic molecule may be 1,000 to 100,000. In addition, the reaction temperature of the dendritic molecule may be 100 to 200° C. When the reaction temperature of the dendritic molecule is 100° C. or less, the polymerization reaction is not satisfactorily performed. On the other hand, when the reaction temperature of the dendritic molecule is 200° C. or more, the reaction product may be degraded.

Subsequently, the solution is added to a large amount of distilled water or methanol to obtain a precipitate. The precipitate is dried to obtain a hyperbranched polymer containing Cu-phthalocyanine or a dendrimer containing Cu-phthalocyanine. Generally, a hyperbranched polymer containing the metal phthalocyanine and dendrimer containing the metal phthalocyanine are simultaneously formed, and thus both are able to be contained in a product. If necessary, the product is dissolved in a mixed solvent of water and ethanol, and ammonia is removed while the mixture is refluxed for 24 hours. The mixed solution is poured into water, and the pH thereof was adjusted to 3-4. As a result, a precipitant can be obtained. The precipitant is washed and dried to obtain a dendritic molecule according to an embodiment of the present invention.

According to an embodiment of the present invention, there is provided an organic light emitting diode including a hole injection layer or a hole transport layer comprising the dendritic molecule.

The organic light emitting diode according to the embodiment of the present invention can have various structures. That is, at least one layer selected from the group consisting of an emissive layer, a hole injection layer, a hole transport layer, a hole blocking layer, an electron blocking layer, an electron transport layer and an electron injection layer can be included between a first electrode and a second electrode.

The organic light emitting diode according to the embodiment of the present invention can be categorized into two types of device, that is, a device employing a polymer emissive layer and a device employing a small-molecule emissive layer.

When the organic light emitting diode according to the embodiment of the present invention employs a polymer emissive layer, the organic light emitting diode includes a first electrode formed on a substrate; a hole injection layer (and/or a hole transport layer) formed on the first electrode; the polymer emissive layer formed on the hole injection layer (or the hole transport layer); and a second electrode formed on the emissive layer.

In the organic light emitting diode employing a polymer emissive layer according to the embodiment of the present invention, the substrate can be any substrate that is used in a conventional organic light emitting diode, and may be a glass substrate or a transparent plastic substrate that has excellent transparency, and surface smoothness, can be easily treated, and is waterproof.

In the organic light emitting diode employing a polymer emissive layer according to the embodiment of the present invention, when the organic light emitting diode has a front emission structure, a metal film, which is a reflexive film, is used as the first electrode formed on the substrate. On the other hand, when the organic light emitting diode has a rear emission structure, the first electrode can comprise ITO, IZO, $SnO_2$, ZnO, or mixtures thereof.

In the organic light emitting diode employing a polymer emissive layer according to the embodiment of the present invention, the hole injection layer (and/or hole transport layer) comprises the dendritic molecule represented by Formula 1.

In the embodiment of the present invention, the hole injection layer and/or the hole transport layer can comprise the dendritic molecule alone, and can be also formed by blending the dendritic molecule with a thermoplastic resin, a thermosetting resin or mixtures thereof.

Examples of the thermoplastic resin may include at least one selected from the group consisting of polyimide, polyamide, polyamide imide, polyether imide, polyester, benzooxazole, polystyrene, polyvinylcarbazole and polymethylmethacrylate, but are not limited thereto.

Examples of the thermosetting resin may include at least one selected from the group consisting of an epoxy resin, a polyimide resin, a cyanate resin, a phenol resin, a benzocyclobutene resin and a dicyclopentadiene resin, but are not limited thereto.

In the embodiment of the present invention, the amount of the thermoplastic resin or the thermosetting resin may be 5 to 90 parts by weight based on 100 parts by weight of the dendritic molecule used in the present invention, and more preferably, 20 to 80 parts by weight. When the amount of the thermoplastic resin or the thermosetting resin is less than 5 parts by weight, the blended resin may have poor mechanical properties. On the other hand, when the amount of the thermoplastic resin or the thermosetting resin is greater than 90 parts by weight, hole injection and transport effects are insufficient.

The dendritic molecule used in the present invention is deposited on the first electrode using a method that is conventionally used in the art to which the present invention pertains, for example, thermal evaporation, spin coating, screen printing, contact printing, transfer printing, inkjet printing, nozzle printing or the like. In particular, the dendritic molecule containing metal phthalocyanine used in the present invention includes a polar group such as a carboxyl group at the end, thereby being able to be dissolved in a polar organic solvent having a boiling point of 50 to 210° C. by 20 weight % or more. Therefore, the dendritic molecule containing metal phthalocyanine can be deposited using a solution casting method by being dissolving in the solvent. Examples of the polar organic solvent can include acetone, tetrahydrofuran (THF), dimethyl acetamide, dimethylformamide, N-methyl-2-pyrolidone or the like.

The thickness of the hole injection layer or the hole transport layer may be in the range of about 10 to 500 Å. When the thickness of the hole injection layer or the hole transport layer is less than 10 Å, the hole injection or transporting ability of the hole injection layer or the hole transport layer may be insufficient. On the other hand, when the thickness of the hole injection layer or the hole transport layer is greater than 500 Å, it is not preferable because of the increase of the driving voltage of the organic light emitting diode.

When the organic light emitting diode according to the embodiment of the present invention uses a polymer emissive layer, the polymer emissive layer can comprise a phosphorous or fluorescent material.

In addition, an electron injection layer (EIL) can be selectively formed on the polymer emissive layer. Nonrestrictive examples of the material used to form the EIL can include LiF, CsF, $BaF_2$, $MgF_2$, NaCl, a lithium quinolate (Liq.), $Cs_2CO_3$, $Al_2O_3$, MgO, $Li_2O$ or a mixture thereof.

The EIL can also comprise an organic small molecular material used to form hole blocking layer (HBL) or an electron transport layer (ETL) together with the EIL forming material mentioned above. Nonrestrictive examples of the organic small molecular material used to form the HBL include phenanthrolines (for example, BCP obtained from UDC), imidazoles (for example, TPBI), triazoles, oxadiazoles (for example, PBD), an aluminum complex (obtained from UDC), BAlq, 4,7-diphenyl-1,10-phenanthrolin (Bphen), which are represented by the following formulae, and the like:

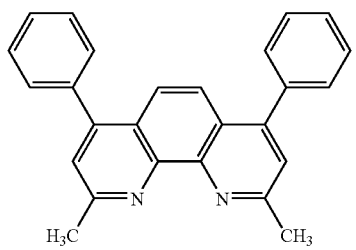

Phenanthroline-containing
organic compound (BCP)

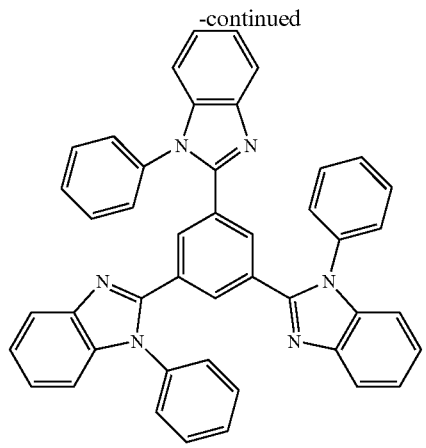

Imidazole-containing organic compound (TPBI)

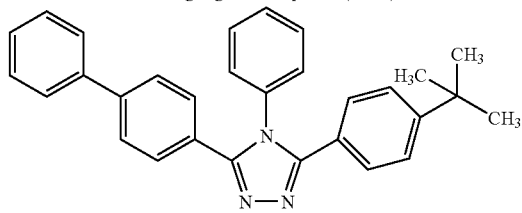

Triazole-containing organic compound

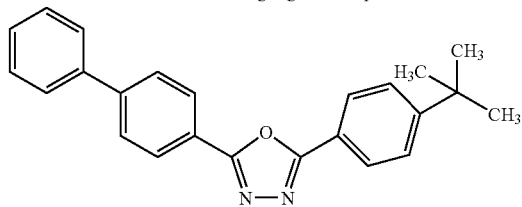

Oxadiazole-containing organic compound (PBD)

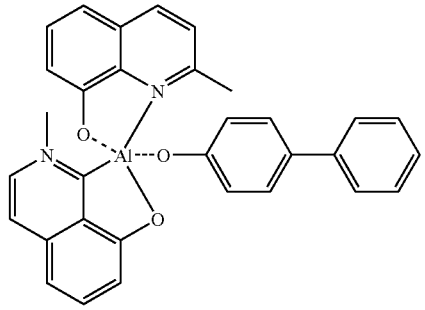

BAlq

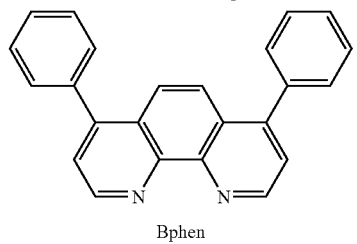

Bphen

Nonrestrictive examples of the organic small molecular material used to form the ETL include oxazoles, isooxazoles, triazoles, isothiazoles, oxadiazoles, thiadiazoles, perylenes, an aluminium complex (for example, tris(8-quinolinolato)-aluminium ($Alq_3$)), BAlq, SAlq, Almq3, a gallium complex (for example, Gaq'2OPiv, Gaq'2OAc, 2(Gaq'2)), BPQ(bis(phenylquinoxaline)), TPQ(starburst tris(phenylquinoxaline)

such as TPQ1 and TPQ2, 1,3,5-triazine, BCP (2,9-Dimethyl-4,7-diphenyl-1,10-phenanhroline), BeBq2(bis(10-hydroxybenzo[h]quinolinato)beryllium), TPBI(2,2',2"-(1,3,5-Benzinetriyl)-tris(1-phenyl-1-H-benzimidazole)), E3(terfluorene), which are represented by the formulae below, and the like:
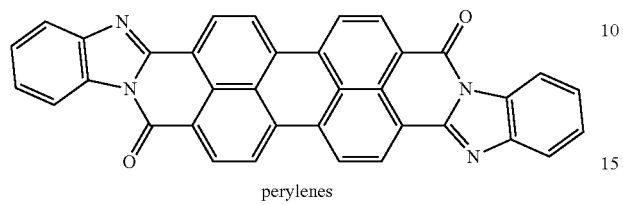
perylenes
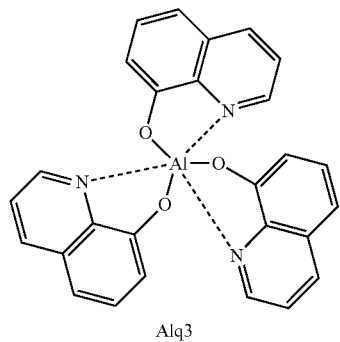
Alq3
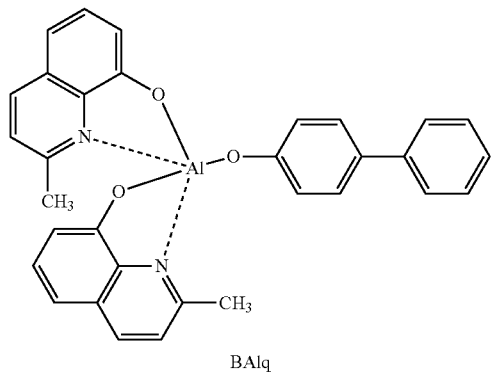
BAlq
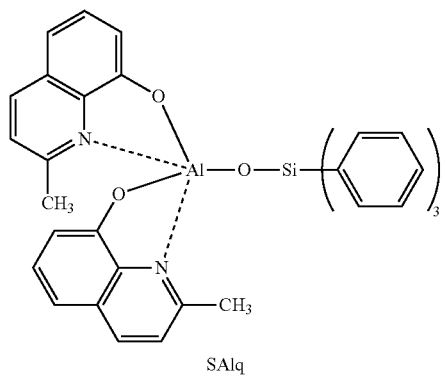
SAlq
-continued
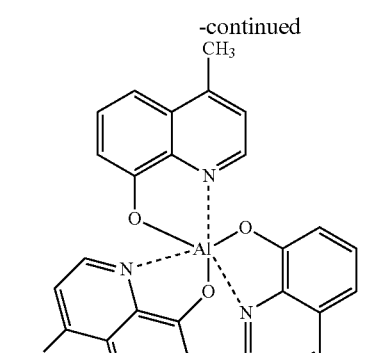
Almq3
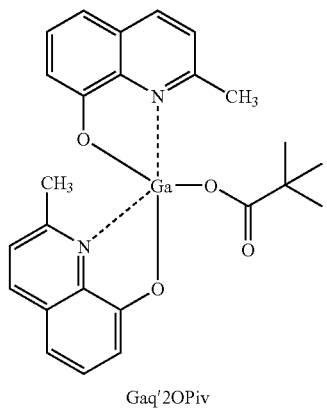
Gaq'2OPiv
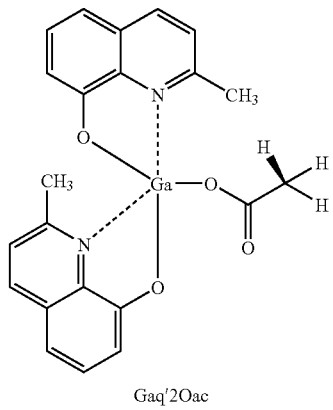
Gaq'2Oac
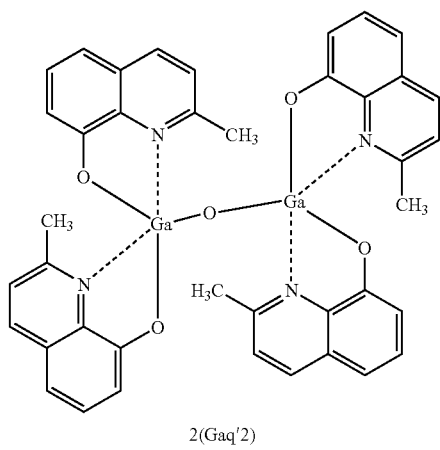
2(Gaq'2)

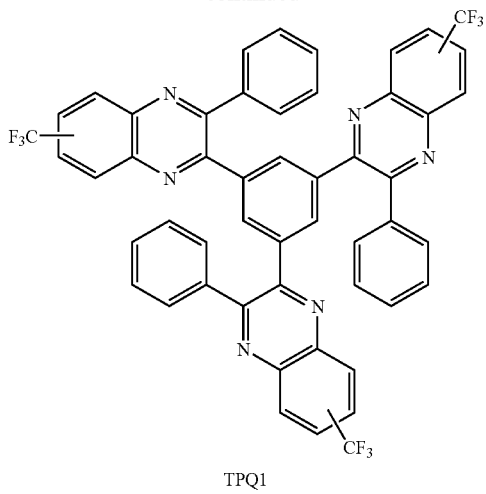

TPQ1

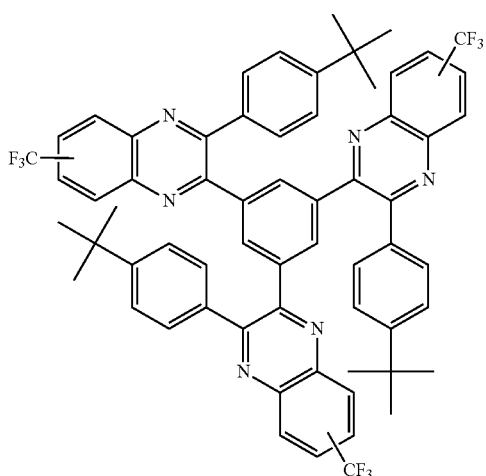

TPQ2

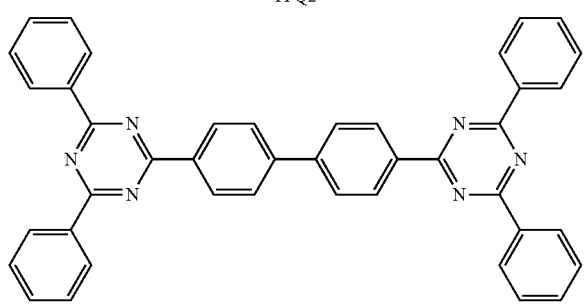

1,3,5-triazine

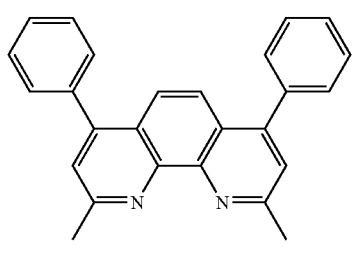

BCP

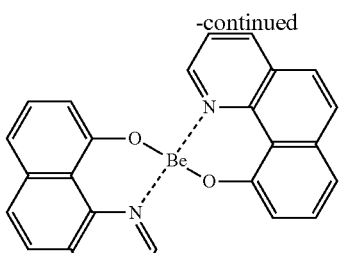

BeBq2

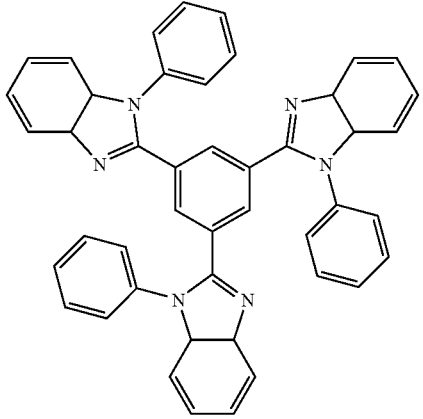

TPBI

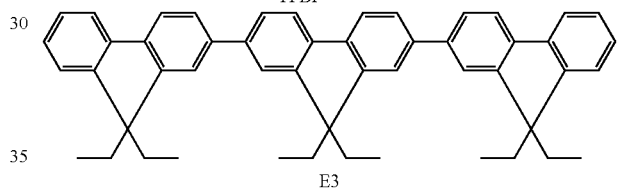

E3

Then, a second electrode is formed on the polymer emissive layer when the organic light emitting diode does not include an electron injection layer, and is formed on an electron injection layer when the organic light emitting diode includes an electron injection layer. The second electrode can comprise alloys of a metal selected from the group consisting of Li, Cs, Ca, Ba, Mg, Al, Ag or Au, or multiple layers of the metal.

When the organic light emitting diode according to the embodiment of the present invention employs a small molecule emissive layer, the organic light emitting diode includes a first electrode formed on a substrate; a hole injection layer formed on the first electrode; the small molecule emissive layer formed on the hole injection layer; an electron injection layer formed on the small molecule emissive layer; and a second electrode formed on the electron injection layer. In addition, the organic light emitting diode can further include at least one organic layer selected from the group consisting of a hole transport layer disposed between the hole injection layer and the small molecule emissive layer, an electrode transport layer disposed between the small molecule emissive layer and the electron injection layer, and a hole blocking layer disposed between the small molecule emissive layer and the electron transport layer.

When the organic light emitting diode according to the embodiment of the present invention employs a small molecule emissive layer, the hole injection layer or the hole transport layer comprises the dendritic molecule represented by Formula 1.

When the organic light emitting diode according to the embodiment of the present invention employs a small molecule emissive layer, the dendritic molecule containing metal phthalocyanine used in the present invention is formed on the first electrode using a method that is conventionally used in the art to which the present invention pertains, for example, thermal evaporation, spin coating, screen printing, contact printing, transfer printing, inkjet printing, nozzle printing or the like. In particular, the dendritic molecule containing metal phthalocyanine used in the present invention can be dissolved in a polar organic solvent having a boiling point of 50 to 210° C. by 20 weight % or more, and thus can be deposited using a solution casting method. Examples of the polar organic solvent can include acetone, tetrahydrofuran (THF), dimethyl acetamide, dimethylformamide, N-methyl-2-pyrolidone and the like.

After an anode comprising ITO or IZO is treated with UV/Ozone and plasma, the dendritic molecule containing metal phthalocyanine is deposited on the anode to form a very clean thin film.

The dendritic molecule containing metal phthalocyanine is bridged to the anode in a sintering process after being deposited, thereby being insoluble in an organic solvent so as to be stable.

The thickness of the hole injection layer or the hole transport layer may be in the range of about 10 to 500 Å. When the thickness of the hole injection layer or the hole transport layer is less than 10 Å, the hole injection or transporting ability of the hole injection layer or the hole transport layer may be insufficient. On the other hand, when the thickness of the hole injection layer or the hole transport layer is greater than 500 Å, it is not preferable because of the increase of the driving voltage of the organic light emitting diode. The substrate and the first electrode can be the same substrate and first electrode as used in the organic light emitting diode using a polymer emissive layer.

In the organic light emitting diode using a small molecule emissive layer, a red emitting material, a green emitting material and a blue emitting material are patterned on R, G and B regions of pixel regions of an emissive layer (EML) on the hole injection layer or the hole transport layer to form an emissive layer (EML). The emitting materials can be a mixture of at least two host materials.

The thickness of the EML may be in the range of about 100 to 800 Å, and preferably, in the range of 300 to 600 Å. When the thickness of the EML is less than 100 Å, the efficiency and lifetime of the organic light emitting diode may be insufficient. On the other hand, when the thickness of the EML is greater than 800 Å, it is not preferable because of the increase of the driving voltage of the organic light emitting diode.

Nonrestrictive examples of the material used to form the HBL include phenanthrolines (for example, BCP obtained from UDC), imidazoles (for example, TPBI), triazoles, oxadiazoles (for example, PBD), an aluminum complex (obtained from UDC), BAlq, 4,7-diphenyl-1,10-phenanthrolin (Bphen), which are represented by the following formulae, and the like:

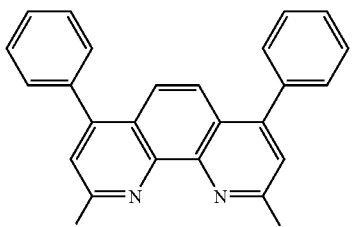
Phenanthroline-containing
Organic compound (BCP)

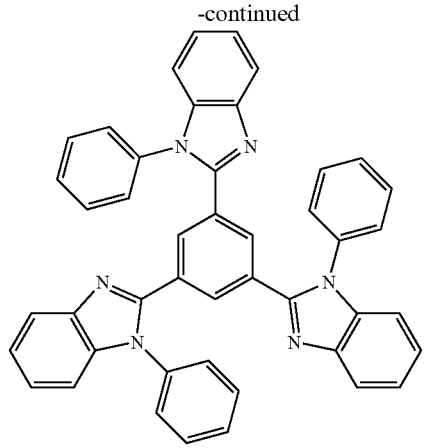
Imidazole-containing organic compound
(TPBI)

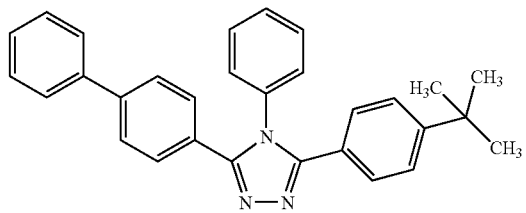
Triazole-containing organic compound

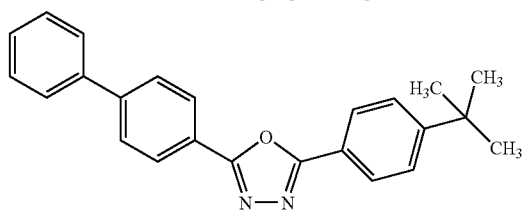
Oxadiazole-containing compound (PBD)

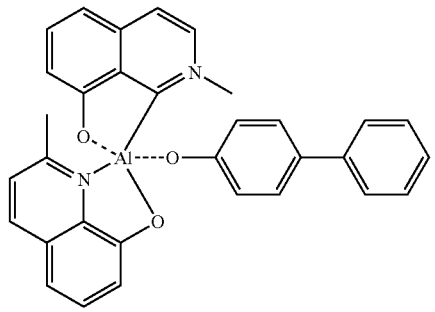
BAlq

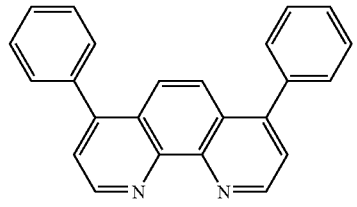
Bphen

The thickness of the HBL may be in the range of about 50 to 300 Å. When the thickness of the HBL is less than 50 Å, the hole blocking ability of the HBL may be insufficient. On the other hand, when the thickness of the HBL is greater than 300 Å, it is not preferable because of the increase of the driving voltage of the organic light emitting diode.

In addition, an electron transport layer (ETL) can be formed on the emissive layer or the hole blocking layer. A material used to form the ETL can be any material that is conventionally used in an ETL. Nonrestrictive examples of the material include oxazoles, isooxazoles, triazoles, isothiazoles, oxadiazoles, thiadiazoles, perylenes, an aluminium complex (for example, tris(8-quinolinolato)-aluminium (Alq3)), BAlq, SAlq, Almq3 (Almq3), a gallium complex (for example, Gaq'2OPiv, Gaq'2OAc, 2(Gaq'2)), bis(phenylquinoxaline) (BPQ), starburst tris(phenylquinoxaline) (TPQ) such as TPQ1 and TPQ2, 1,3,5-triazine, BCP (2,9-Dimethyl-4,7-diphenyl-1,10-phenanhroline), BeBq2(bis(10-hydroxybenzo[h]quinolinato)beryllium), TPBI(2,2',2"-(1,3,5-Benzinetriyl)-tris(1-phenyl-1-H-benzimidazole)), E3(terfluorene), which are represented by the following formulae, and the like:

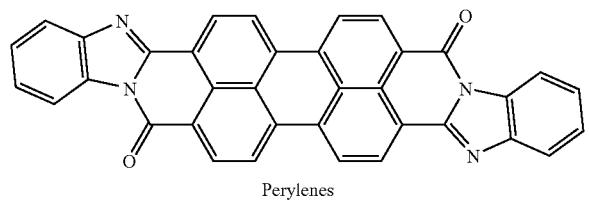

Perylenes

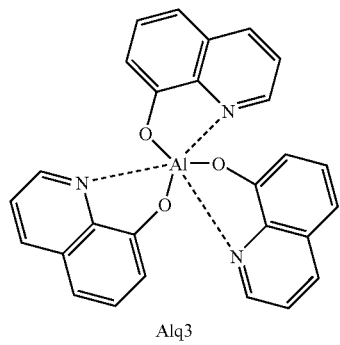

Alq3

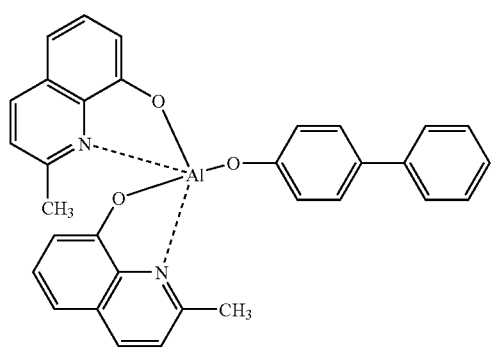

BAlq

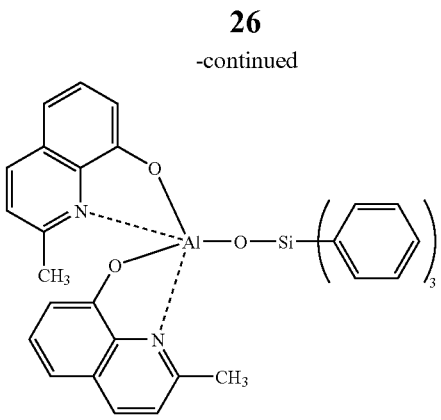

SAlq

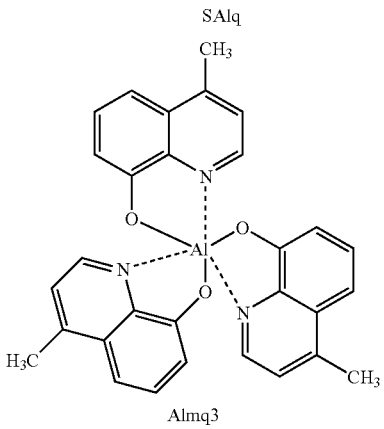

Almq3

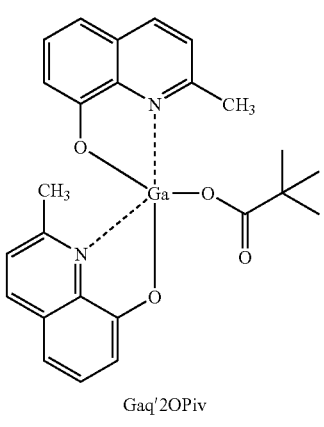

Gaq'2OPiv

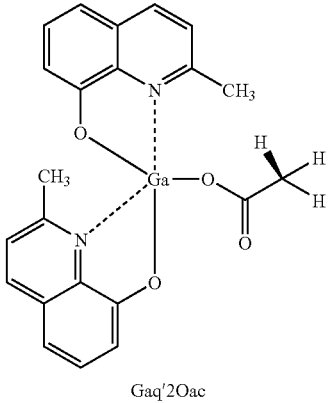

Gaq'2Oac

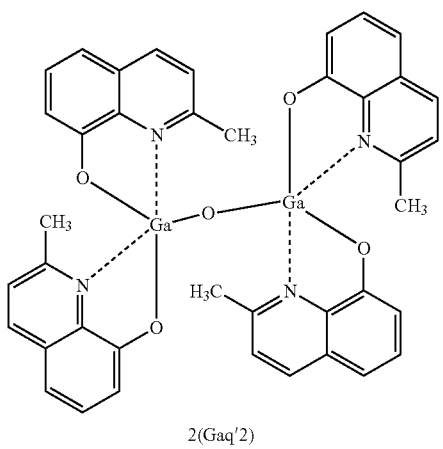

2(Gaq'2)

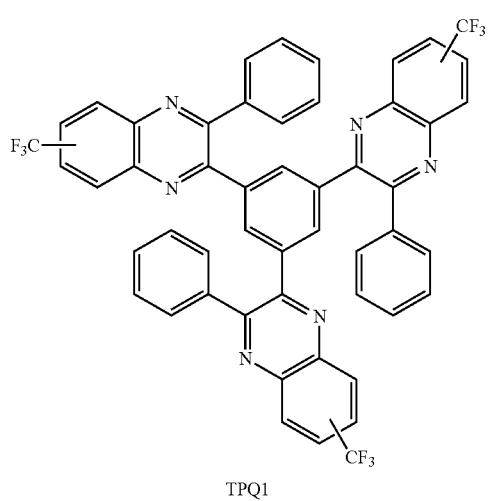

TPQ1

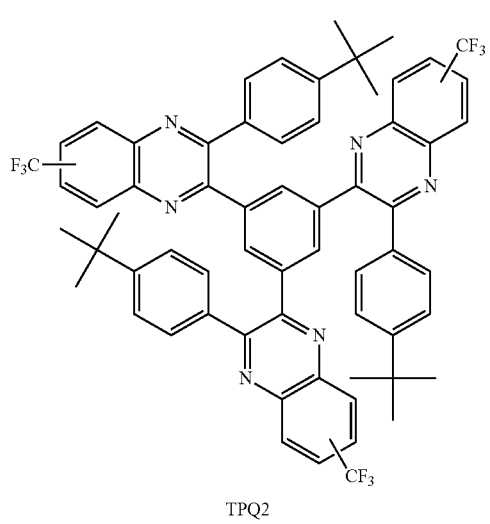

TPQ2

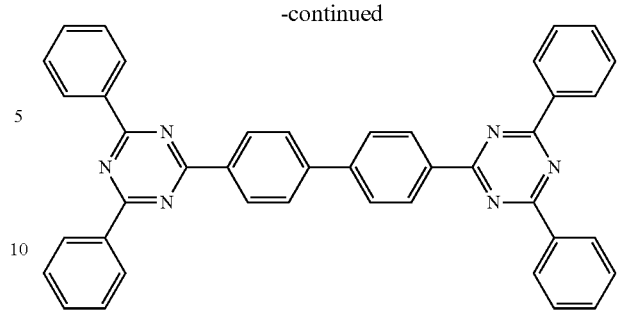

1,3,5-triazine

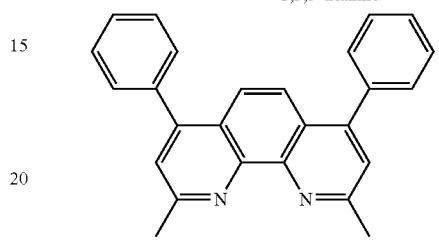

BCP

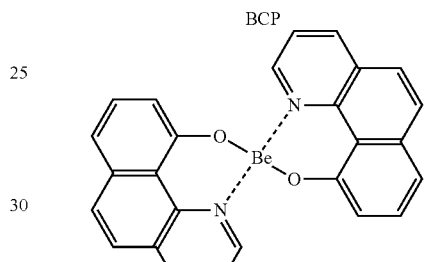

BeBq2

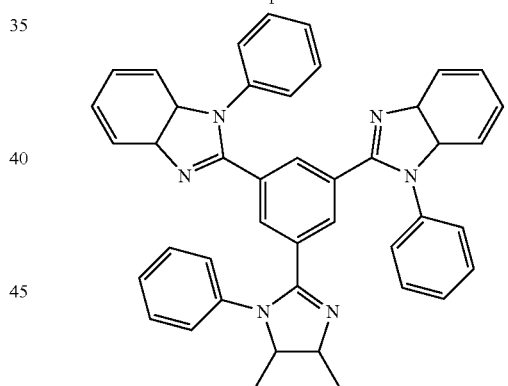

TPBI

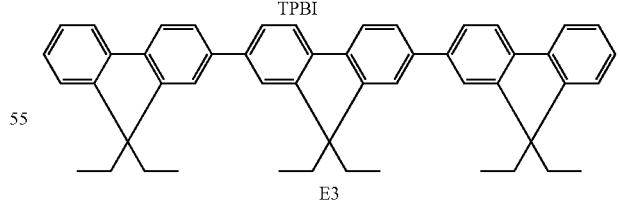

E3

The thickness of the ETL may be in the range of 50 to 600 Å. When the thickness of the ETL is less than 50 Å, the efficiency and lifetime of the organic light emitting diode are reduced. On the other hand, when the thickness of the ETL is greater than 600 Å, it is not preferable because of the increase of the driving voltage of the organic light emitting diode.

In addition, an electron injection layer (EIL) can be selectively formed on the ETL. The material used to form the EIL is not particularly limited, and can be LiF, CsF, $BaF_2$, $MgF_2$, NaCl, Liq, $Cs_2CO_3$, $Al_2O_3$, MgO, $LiO_2$ or the like. The thickness of the EIL may be in the range of 1-100 Å. When the thickness of the EIL is less than 1 Å, the EIL cannot effectively perform its function so that the driving voltage of the organic light emitting diode increases. On the other hand, when the thickness of the EIL is greater than 100 Å, the EIL acts as an insulating layer so that the driving voltage of the organic light emitting diode may increase.

Lastly, a metal for a second electrode is deposited on the ETL. The metal for the second electrode can be Li, Mg, Al, Al—Li, Ca, Mg—In, Mg—Ag or the like.

Up to now, an organic light emitting diode including a hole injection layer or a hole transport layer comprising the dendritic molecule containing metal phthalocyanine of the present invention has been described. Since the hole injection layer or hole transport layer comprises the dendritic molecule having a metal such as copper at a core portion thereof, the organic light emitting diode can have a high work function, high emitting efficiency and high luminance. In addition, since the hole injection layer or a hole transport layer is formed using a solution process that uses an organic solvent, the organic light emitting diode can be easily manufactured while water can be avoided completely. Furthermore, the dendritic molecule containing metal phthalocyanine improves adhesiveness between the hole injection layer and an electrode.

The present invention will now be described in greater detail with reference to the following examples. The following examples are for illustrative purposes only and are not intended to limit the scope of the invention.

EXAMPLES

Example 1

Synthesis of Dendritic Molecule

Dimethyl sulfoxide (DMSO) and N,N'-dimethylacetamide (DMAC) were dried with calcium hydride and distilled under subatmosphere pressure in advance before use. Unless particularly specified here, all the reagents except the two compounds were used as they were.

The obtained intermediates and final products were analyzed using an analyzer such as IR, NMR, TGA, GPC or the like. A FTIR-8100 Fourier transform infrared spectrophotometer obtained from Shimadzu Co. was used to obtain IR spectra. A JNM-AL 300 MHz spectrophotometer obtained from JEOL Co. Ltd. was used to obtain NMR spectra. Thermogravimetric analysis (TGA) was performed using a TG/DTA 6200 obtained from Seiko Co. by heating at a speed of 10° C./minute in an air atmosphere. Gel permeation chromatography (GPC) was performed using a Shodex RI-71 refractive index detector. In addition, dimethylformamide (DMF) containing 0.01 M of lithium bromide was used.

The following reaction scheme represents a method of preparing a dendritic molecule of Example 1.

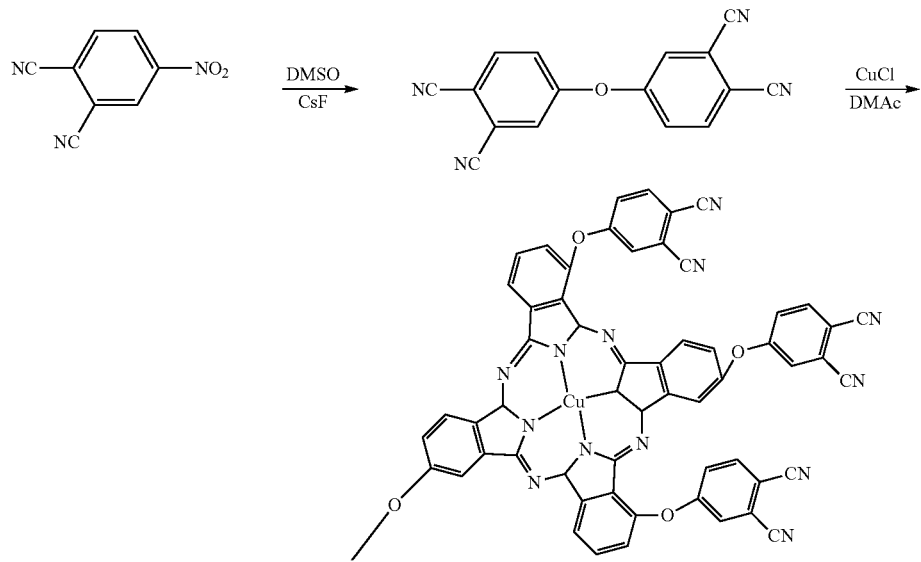

Reaction Scheme

-continued
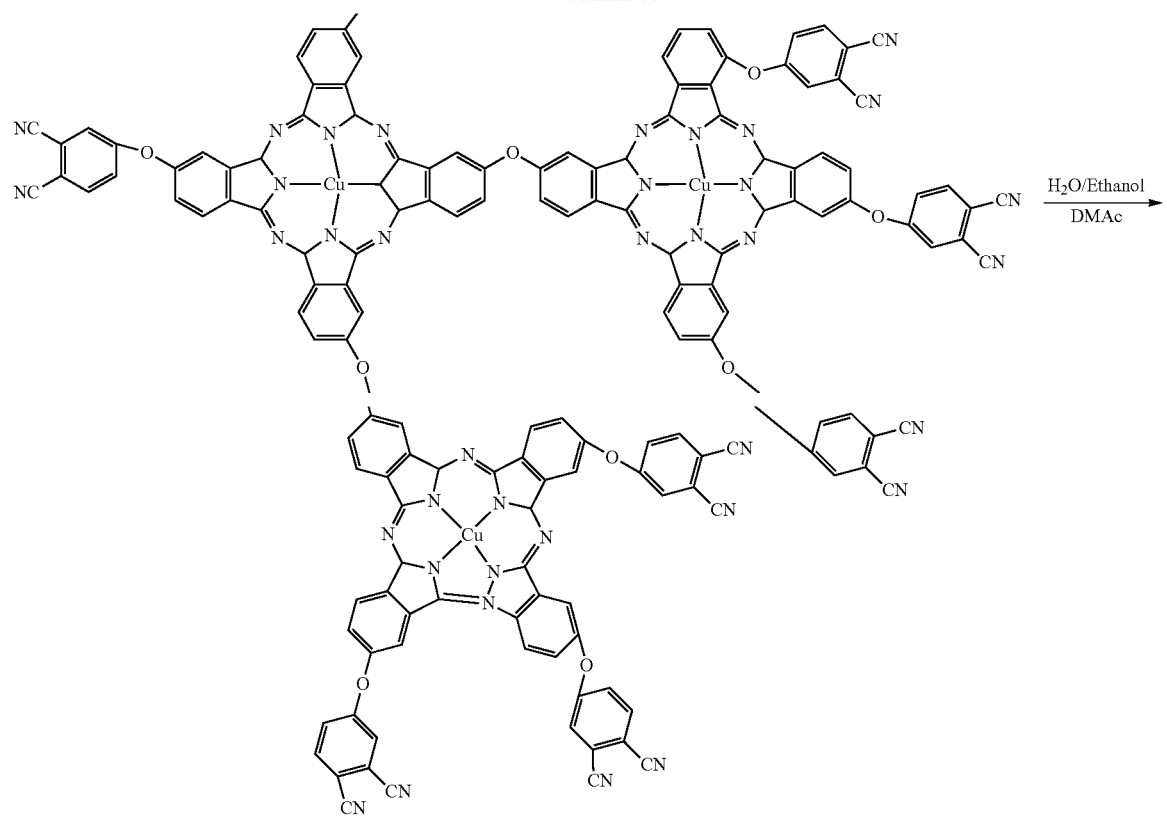
$\xrightarrow{\text{H}_2\text{O/Ethanol}}{\text{DMAc}}$
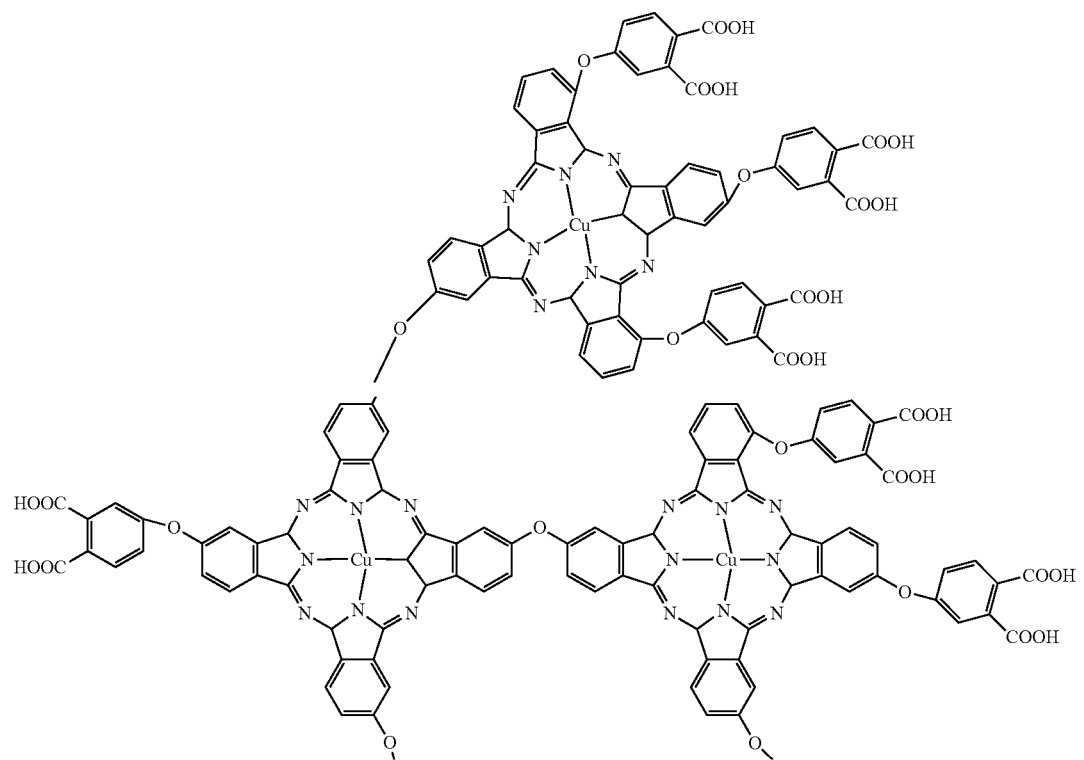

-continued

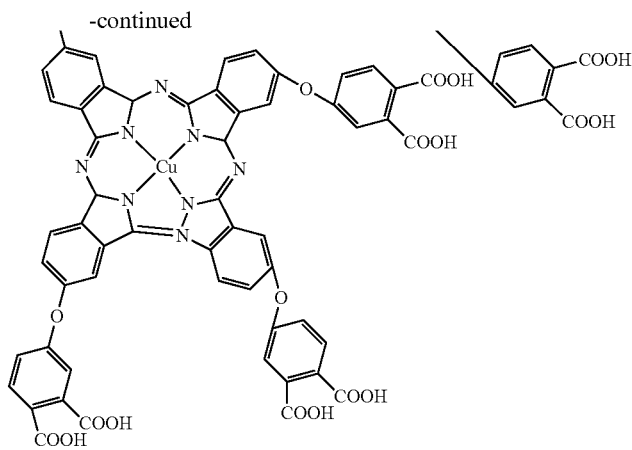

a. Synthesis of 4'4-oxybis(phthalonitrile)

7.27 g of 4-nitrophthalonitrile (40 mmol) was added to a flask and dissolved in 60 ml of dimethyl sulfoxide (DMSO). Then, 11.04 g of cesium fluoride (80 mmol) was added to the flask and then the mixture was stirred at room temperature for 48 hours. The reacted mixed solution was poured into 1,000 ml of water. The obtained crude product was filtered, and the resultant was washed with water and then vacuum dried. The solid was recrystallized with methanol and vacuum dried to obtain 4.21 g of yellow powder-type 4'4-oxybis(phthaloni-trile). The yield of the 4'4-oxybis(phthalonitrile) was 72%, and the results of chemical analysis are as follows:

mp: 254° C.

$^1$H NMR (ppm): 8.24-8.21 (d, 2H); 8.04 (d, 2H); 7.72-7.68 (t, 2H).

$^{13}$C NMR (ppm): 158.4; 136.6; 124.7; 124.7; 117.1; 115.7; 115.2; 110.6.

IR (KBr, cm$^{-1}$): 3433, 3102, 3073, 3039, 2924, 2233, 1727, 1588, 1568, 1483, 1418, 1309, 1278, 1251, 1203, 1093, 968, 906, 852, 528.

b. Preparation of Dendritic Molecule Containing Cu-phthalocyanine (CuPc) Having a CN Terminal Group 1.21 g of the obtained 4'4-oxybis(phthalonitrile) (4.5 mmol) and 0.14 g of CuCl (1.5 mmol) were added to a flask and dissolved in 40 ml of DMAc. The mixed solution was stirred at 160° C. for 8 hours. The mixed solution was poured into 800 ml of water. The obtained crude product was filtered, and the resultant was washed with water and then vacuum dried. The solid was refluxed with methanol two times, and then filtered and washed with cold methanol three times. The obtained blue powder-type solid was vacuum dried to obtain 0.88 g of a dendritic molecule containing CuPc having a CN terminal group. The yield of the dendritic molecule was 54% and the results of chemical analysis of the polymer are as follows:

$^1$H NMR (ppm): 8.24-8.21 (d); 8.04 (s); 7.71-7.69(q)7.57-7.54(d). 7.53-7.42(s).

IR (KBr, cm$^{-1}$): 3324, 3103, 3074, 3040, 2358, 2337, 2234, 1956, 1774, 1723, 1589, 1568, 1484, 1418, 1358, 1310, 1280, 1251, 1202, 1168, 1093, 968, 926, 905, 851, 755, 724, 701.

c. Synthesis of Dendritic Molecule Containing CuPc Having a COOH Terminal Group 1 g of the dendritic molecule obtained in operation b and 0.1 g of potassium hydroxide (10 weight %) were added to a 200 ml flask and dissolved in 120 ml of a mixed solvent of water and ethanol (volume ratio=1:1). The mixed solution was refluxed for 24 hours until an ammonia gas, which was a byproduct, was not generated any more. The transparent deep blue solution was poured into 300 ml of water, and adjusted to have a pH of 3-4. The deep blue precipitant was filtered, and the resultant was washed with a dilute hydrochloric acid and water. 0.65 g of the product was obtained and the results of chemical analysis of the product results are as followings:

$^1$H NMR (ppm): 8.24-8.21 (d); 8.04 (s); 7.71-7.69(q)7.57-7.54(d). 7.53-7.42(s).

IR (KBr, cm$^{-1}$): 3377, 2914, 2647, 1646, 1534, 1470, 1224, 1105, 1043, 999, 834, 702, 625, 574, 544.

UV-vis(nm): Imax: 676 nm.

TGA: 382° C. (10% weight loss).

GPC: Mw=11,462, Mn=7,692, Mw/Mn=1.49

The amount of the CuPc unit of the dendritic molecule was 7% as a result of the calculation as below:

The permittivity ($\epsilon$) of CuPc itself was 281. The permittivity ($\epsilon$) of the CuPc unit of the dendritic molecule was calculated as 267. The E value of the CuPc unit of the obtained dendritic molecule was measured as 19 by UV-vis spectrum. The amount of the CuPc unit of the dendritic molecule is calculated using the following formula.

Amount of CuPc of dendritic molecule=(measured $\epsilon$ value)/(calculated $\epsilon$ value)×100

Example 2

Synthesis of Dendritic Molecule

A dendritic molecule was prepared in the same manner as in Example 1, except that the reaction in operation b was performed for 4 hours.

Example 3

Synthesis of Dendritic Molecule

A dendritic molecule was prepared in the same manner as in Example 1, except that the reaction in operation b was performed for 2 hours.

Example 4

Manufacture of Organic Light Emitting Diode

A 15 Ω/cm$^2$ (1600 Å) ITO glass substrate was cut to a size of 50 mm×50 mm×0.7 mm, microwave washed with a neutral detergent solution, pure water and isopropyl alcohol for 5 minutes each, respectively, and then washed with UV ozone for 30 minutes to form a first electrode.

The dendritic molecule containing metal phthalocyanine of Example 1 was dissolved in dimethylformamide, which is an organic solvent, to have an amount of 0.5 weight % based on the total amount of the organic solvent. The dendritic molecule containing metal phthalocyanine was spin coated to have a thickness of 5 nm, and heat treated at 135° C. for 50 minutes to form a hole injection layer. Subsequently, an emissive layer comprising $Alq_3$ was formed on the hole injection layer to have a thickness of 60 nm.

Figure 2:
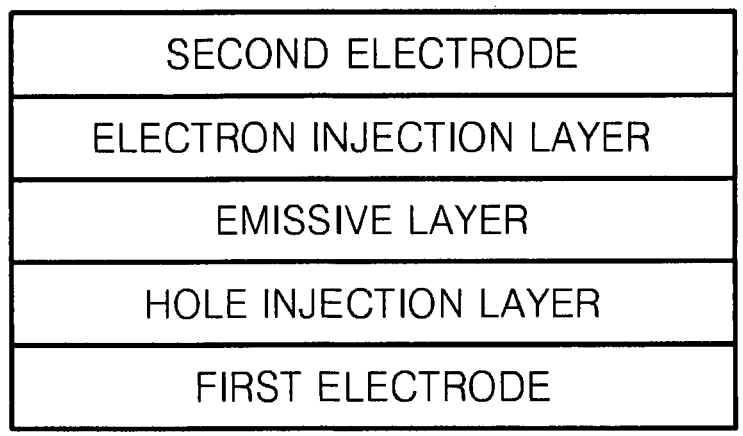
FIG. 2 is a schematic diagram illustrating the structure of an organic light emitting diode according to an embodiment of the present invention.

Then, a second electrode was formed by sequentially vacuum depositing LiF and Al on the emissive layer to have thicknesses of 1 nm and 200 nm, respectively. As a result, an organic light emitting diode as illustrated in FIG. 2 was manufactured.

Example 5

Manufacture of Organic Light Emitting Diode

An organic light emitting diode was manufactured in the same manner as in Example 4, except that the dendritic molecule containing metal phthalocyanine of Example 2 was used to form a hole injection layer.

Example 6

Manufacture of Organic Light Emitting Diode

An organic light emitting diode was manufactured in the same manner as in Example 4, except that the dendritic molecule containing metal phthalocyanine of Example 3 was used to form a hole injection layer.

Comparative Example 1

Manufacture of Organic Light Emitting Diode

An organic light emitting diode was manufactured in the same manner as in Example 4, except that Baytron P AI 4083(PEDOT/PSS amount ratio=1:6) obtained from H.C. Starck Inc. was used to form a hole injection layer.

Comparative Example 2

Manufacture of Organic Light Emitting Diode

An organic light emitting diode was manufactured in the same manner as in Example 4, except that a hole injection layer was not formed.

Performance Evaluation

A work function was measured using a Surface Analyzer (UV/Vis Photoelectron Spectrometer for use in air, Riken Keiki, Model: AC2). The work function of a hole injection layer comprising AI4083 of Comparative Example 1 was 5.18 eV. The work function of the hole injection layer comprising the dendritic molecule containing metal phthalocyanine of Examples 4 through 6 was 5.28 eV.

Figure 3:
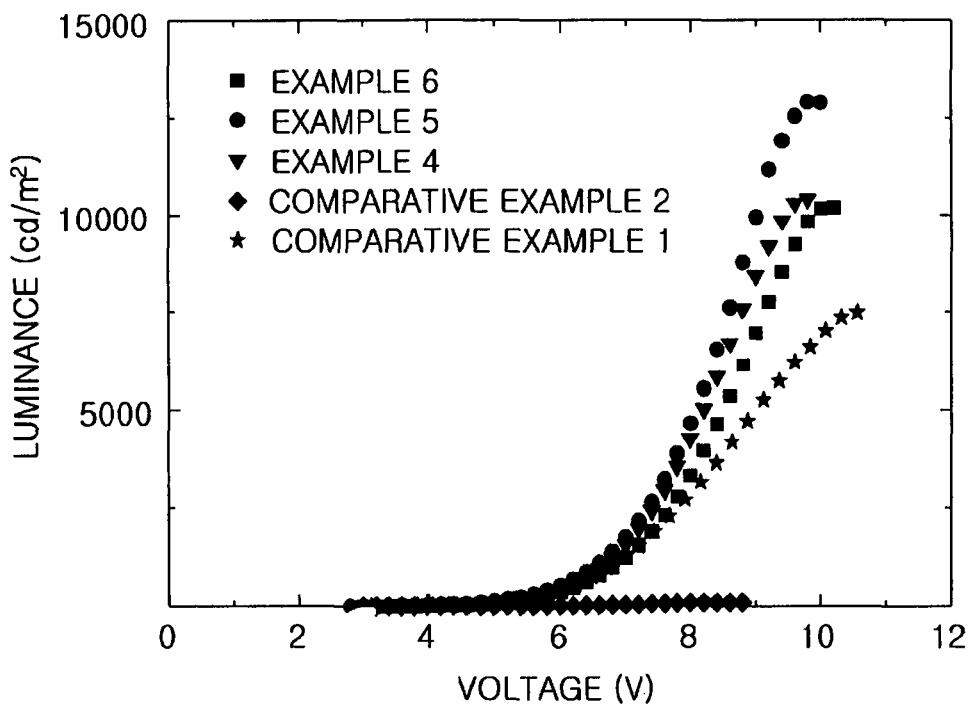
FIG. 3 is a graph showing luminance with respect to voltage of organic light emitting diodes of Examples 4 through 6 and Comparative Examples 1 and 2.
Figure 4:
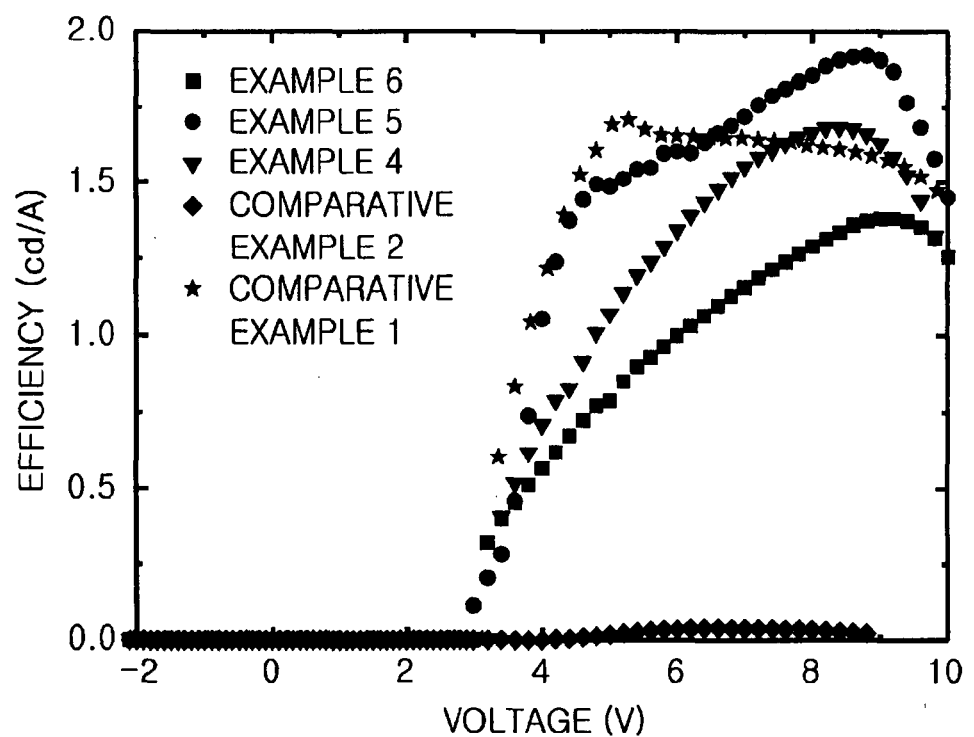
FIG. 4 is a graph showing emitting efficiency with respect to voltage of organic light emitting diodes of Examples 4 through 6 and Comparative Examples 1 and 2.

FIG. 3 is a graph showing luminance with respect to voltage of the organic light emitting diodes of Examples 4 through 6 and Comparative Examples 1 and 2, and FIG. 4 is a graph showing emitting efficiency with respect to voltage of the organic light emitting diodes of Examples 4 through 6 and Comparative Examples 1 and 2.

Referring to FIG. 3, in the case of the organic light emitting diode of Comparative Example 2 that did not use a hole injection layer, the organic light emitting diode had a maximal luminance of 102 $cd/m^2$, and in the case of the organic light emitting diode of Comparative Example 1 that had a hole injection layer comprising a conventional PEDOT/PSS, the organic light emitting diode had a maximal luminance of 7480 $cd/m^2$. However, when a hole injection layer was formed using the dendritic molecule containing metal phthalocyanine used in the present invention, as in Example 5, the organic light emitting diode exhibited a maximal luminance of 12,910 $cd/m^2$.

As can be seen in FIG. 4, the organic light emitting diode of Example 5 having an emitting efficiency of 1.92 cd/A had a higher emitting efficiency compared with the organic light emitting diode of Comparative Example 2 that did not include a hole injection layer. In addition, the organic light emitting diode of Example 5 had a higher emitting efficiency compared with an organic light emitting diode including a hole injection layer comprising the commercially available PEDOT/PSS.

The dendritic molecule used in the present invention can be dissolved in an organic solvent. Therefore, when an organic light emitting diode is manufactured, the dendritic molecule can be easily deposited using a solution deposition method in a glove box to form a hole injection layer or a hole transport layer while moisture can be avoided completely. In addition, an aromatic ring, which is a terminal group of metal phthalocyanine that is included in the dendritic molecule, contains a chemical group such as CN, COOH, $SO_3H$ or $PO_3H$, and thus adhesion to an electrode is improved and film coating properties are excellent. The hole injection layer comprising the dendritic molecule of the embodiment of the present invention has a work function of about 5.28 eV which is higher than that of conventional PEDOT/PSS. Accordingly, it can be seen that a hole injection layer comprising the dendritic molecule of the present invention has more enhanced hole injection ability. Furthermore, an organic light emitting diode comprising the dendritic molecule according to the present invention has high luminance and emitting efficiency.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A dendritic molecule obtained from reacting a compound represented by Formula 3 and a metal or a metal compound, and optionally replacing CN group with R which is selected from the group consisting of COOH, $SO_3H$ and $PO_3H$, the dendritic molecule including metal phthalocyanine represented by Formula 2:

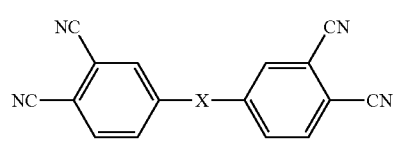

(3)

where X is a bivalent linking group selected from the group consisting of $CH_2$, $SO_2$ and NHCO;

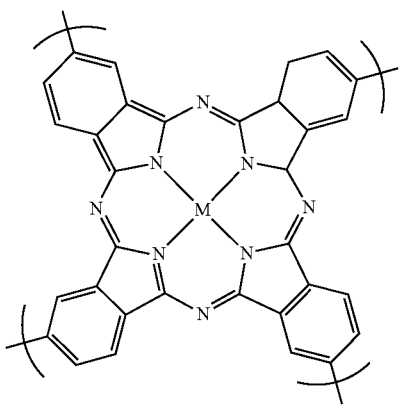

(2)

where M is a core metal of the dendritic molecule.

2. The dendritic molecule of claim 1, wherein the metal or the metal compound includes a metal element selected from the group consisting of Cu, Co, Ni, Ti, Fe, Ru and Zn.

3. A dendritic molecule represented by Formula 1:

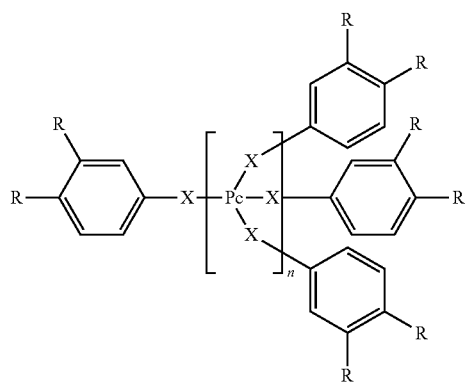

(1)

where Pc is metal phthalocyanine represented by Formula 2:

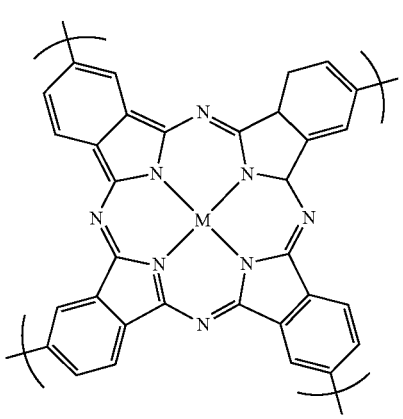

(2)

where M is a core metal of the dendritic molecule;
n is an integer in the range of 2 to 50;

each of the Xs is a bivalent linking group independently selected from the group consisting of $CH_2$, CO, $SO_2$ and NHCO; and each of the Rs is independently selected from the group consisting of CN, COOH, $SO_3H$ and $PO_3H$.

4. The dendritic molecule of claim 3, wherein the core metal M of the metal phthalocyanine of Formula 2 is selected from the group consisting of Cu, Co, Ni, Ti, Fe, Ru and Zn.

5. The dendritic molecule of claim 3, wherein the core metal M is Cu, and all of the Rs are COOH.

6. The dendritic molecule of claim 1, represented by one of the below Formulae:

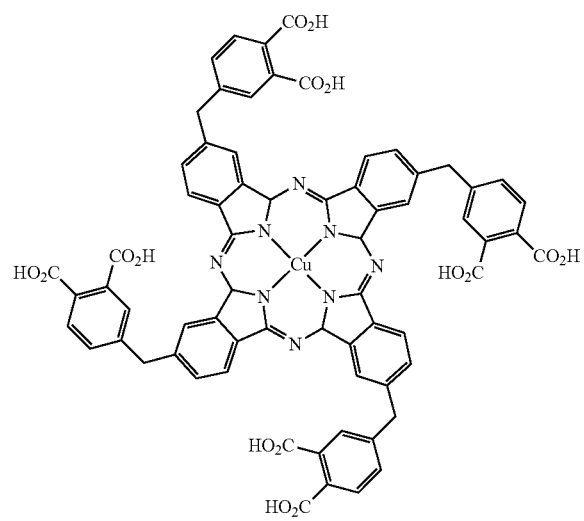

(4B)

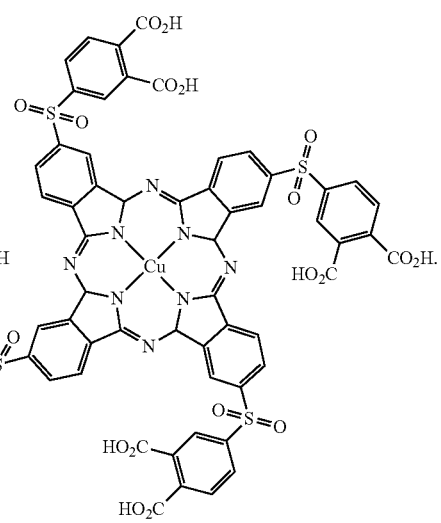

(4E)

7. A dendritic molecule represented by one of Formulae 5 and 6:
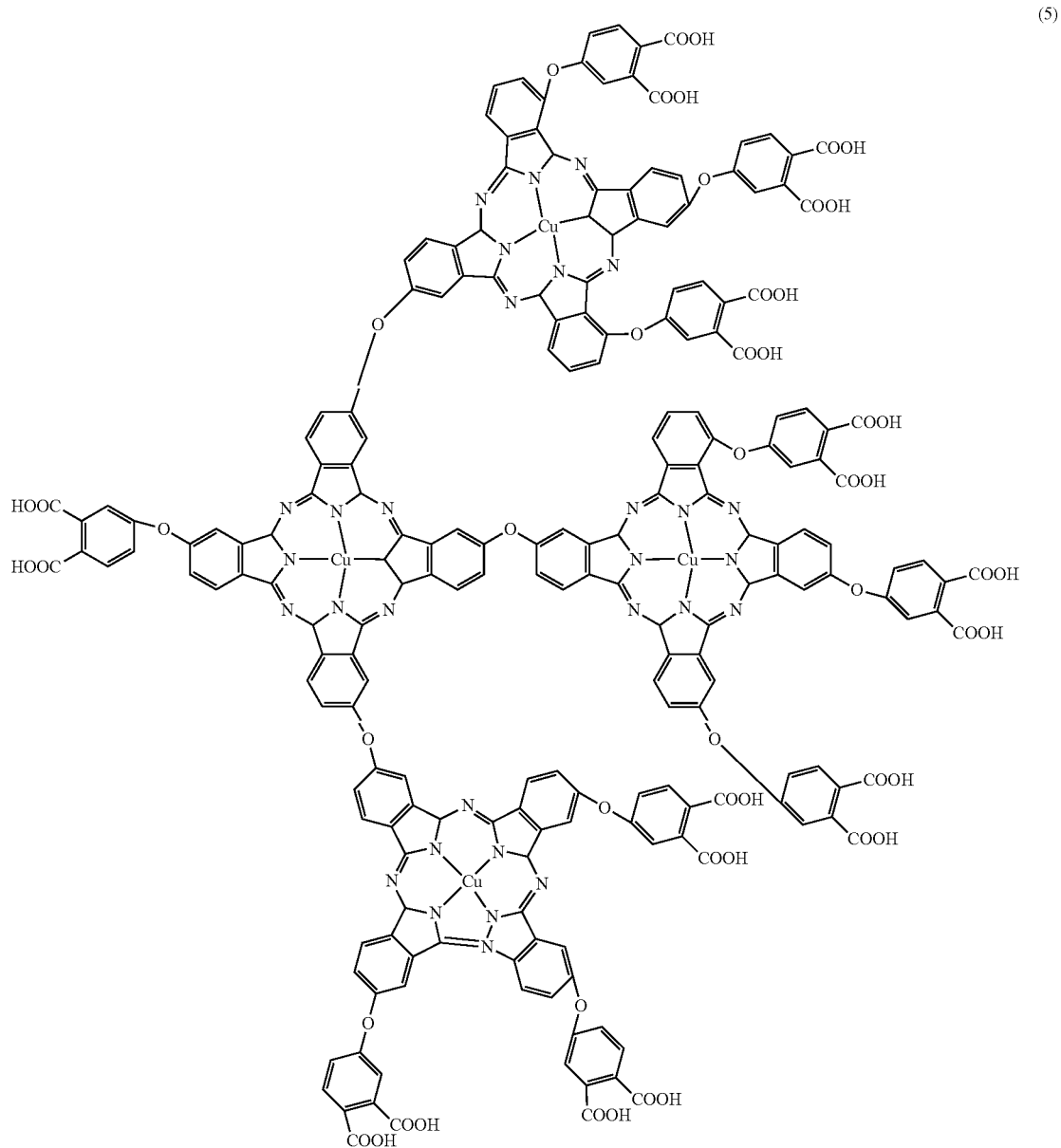
(5)

(6)
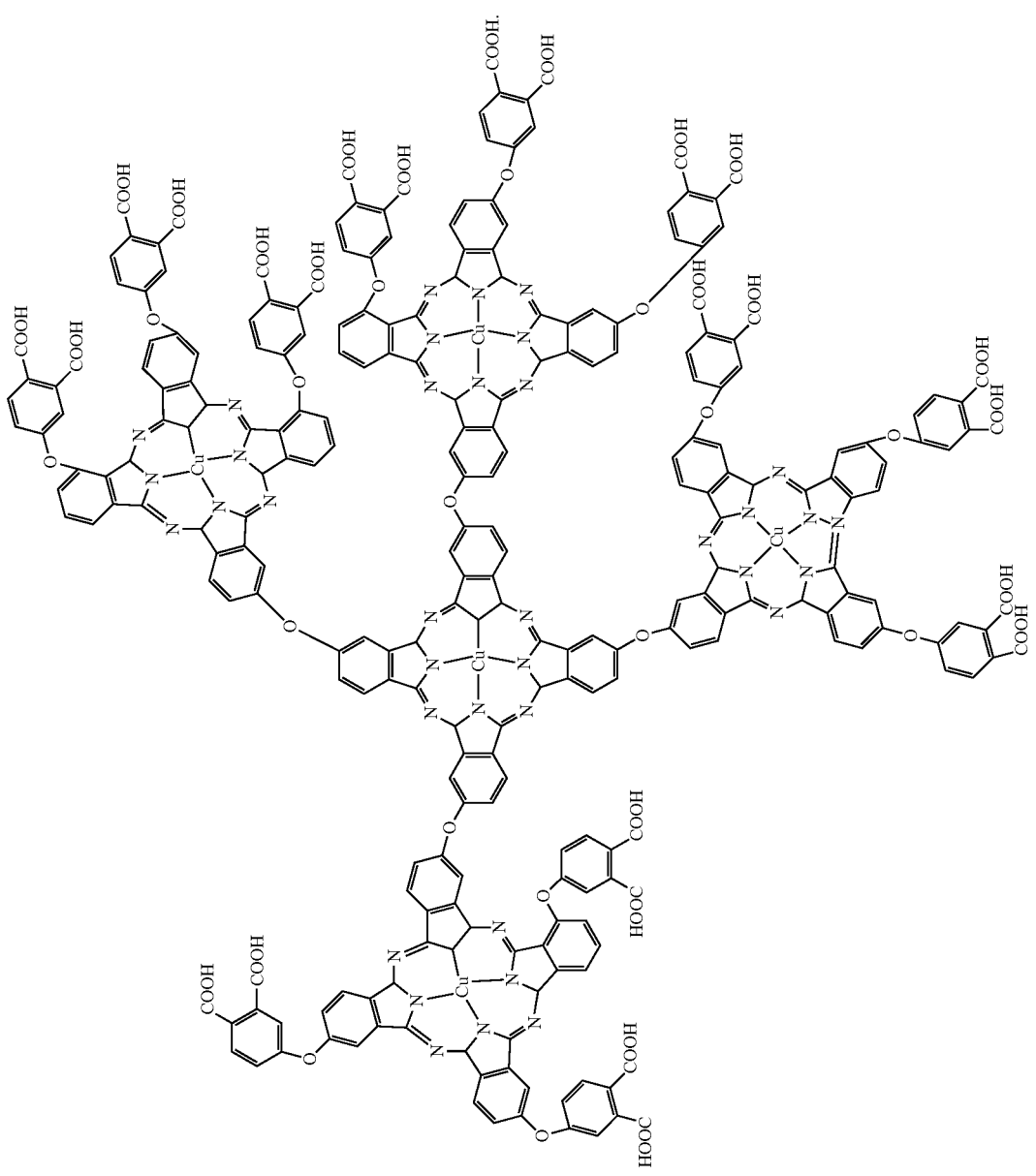

8. The dendritic molecule of claim 7, represented by Formula 6:
(6)
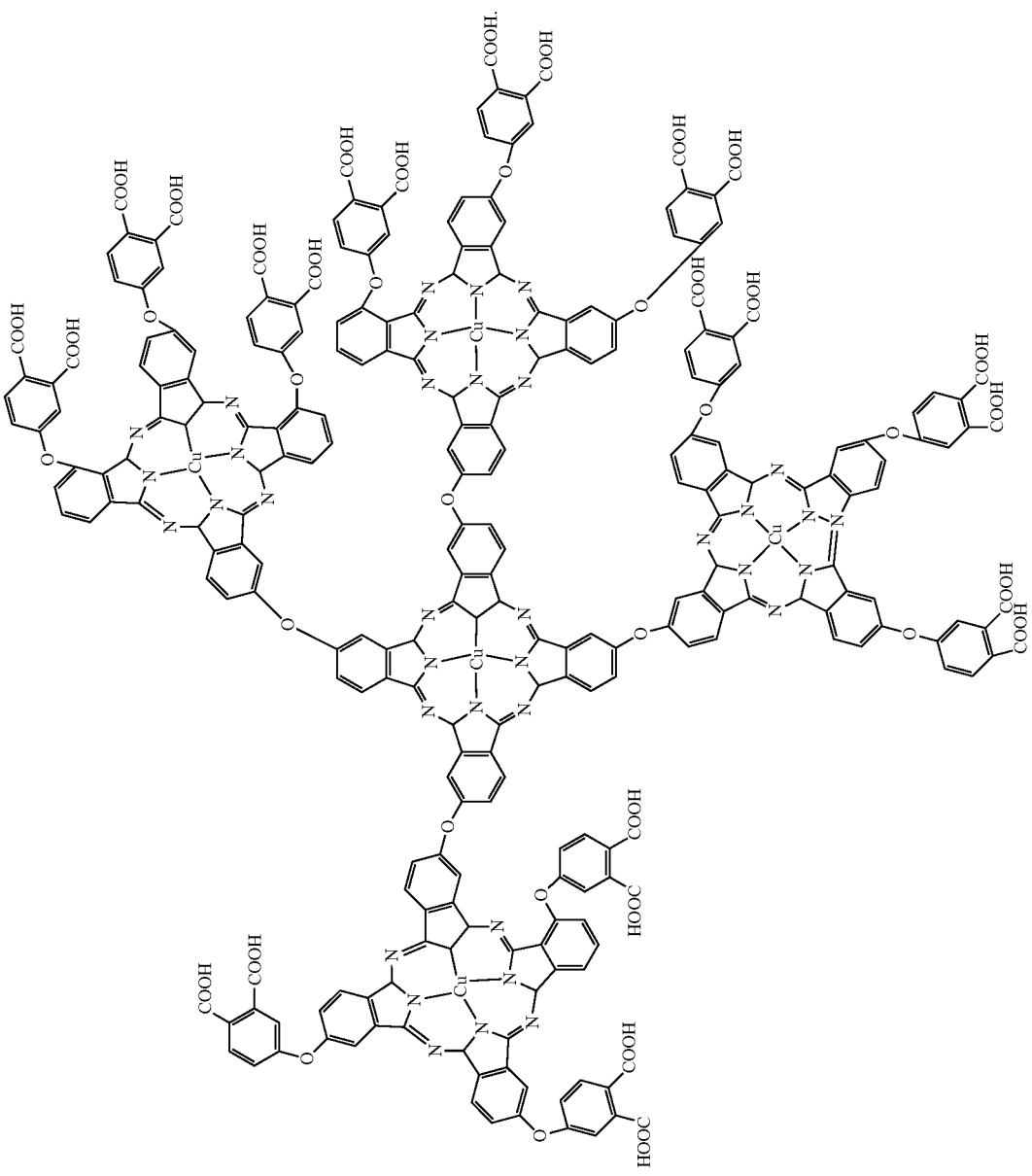

9. The dendritic molecule of claim 1, having a molecular weight of 1,000 to 100,000.

10. An organic light emitting diode, comprising:
a first electrode;
a second electrode facing the first electrode; and
an organic layer interposed between the first electrode and the second electrode, the organic layer comprising a layer comprised of a dendritic molecule represented by Formula 1:

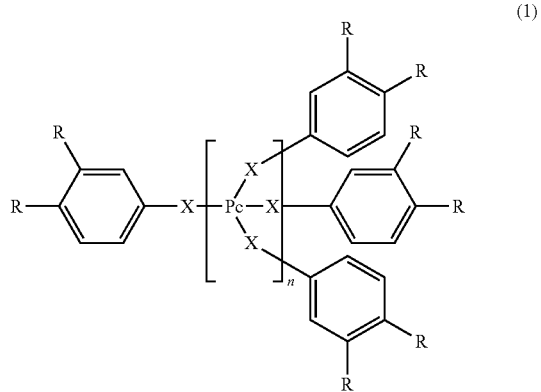

(1)

where Pc is metal phthalocyanine represented by Formula 2:

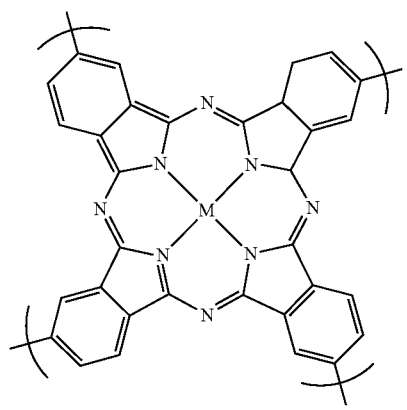

(2)

where M is a core metal of the dendritic molecule;
n is an integer in the range of 1 to 50;
each of the Xs is a bivalent linking group independently selected from the group consisting of O, S, $CH_2$, CO, $SO_2$ and NHCO; and
each of the Rs is independently selected from the group consisting of CN, COOH, $SO_3H$ and $PO_3H$; and
wherein the layer comprised of the dendritic molecule represented by Formula 1 is a buffer layer, a hole injection layer or a hole transport layer.

11. The organic light emitting diode of claim 10, wherein the metal or the metal compound includes a metal element selected from the group consisting of Cu, Co, Ni, Ti, Fe, Ru and Zn.

12. The organic light emitting diode of claim 10, further comprising at least one layer selected from the group consisting of an emissive layer, a hole injection layer, a hole transport layer, an electron blocking layer, a hole blocking layer, an electron transport layer and an electron injection layer, disposed between the first electrode and the second electrode.

13. The organic light emitting diode of claim 10, wherein the organic layer has a structure selected from the group consisting of a stacked structure of a hole injection layer and an emissive layer, a stacked structure of a hole injection layer, an emissive layer and an electron injection layer, a stacked structure of a hole injection layer, a hole transport layer and an emissive layer, a stacked structure of a hole injection layer, a hole transport layer, an emissive layer and an electron injection layer, a stacked structure of a hole injection layer, a hole transport layer, an emissive layer, an electron transport layer and an electron injection layer, and a stacked structure of a hole injection layer, a hole transport layer, an emissive layer, a hole blocking layer, an electron transport layer and an electron injection layer.

14. The organic light emitting diode of claim 10, wherein the dendritic molecule is represented by one of Formulae 4A through 4H:

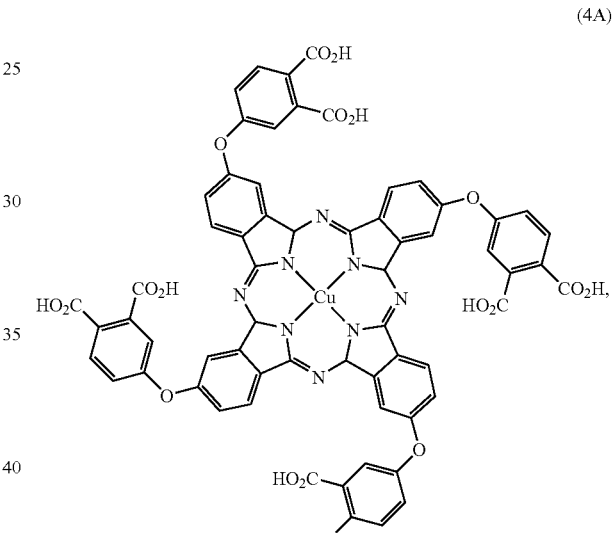

(4A)

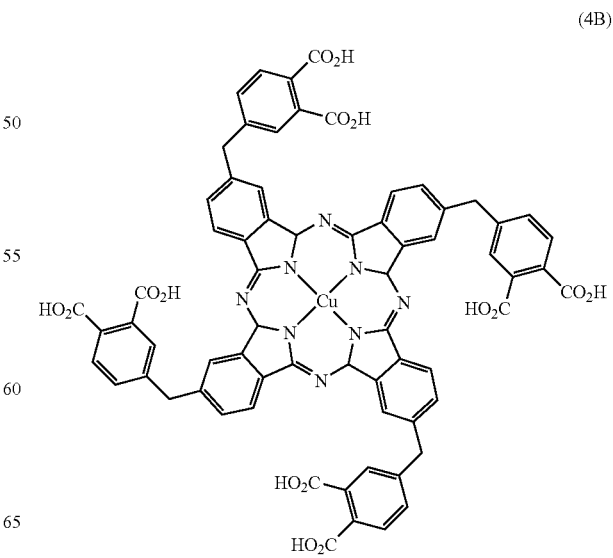

(4B)

-continued
(4C)
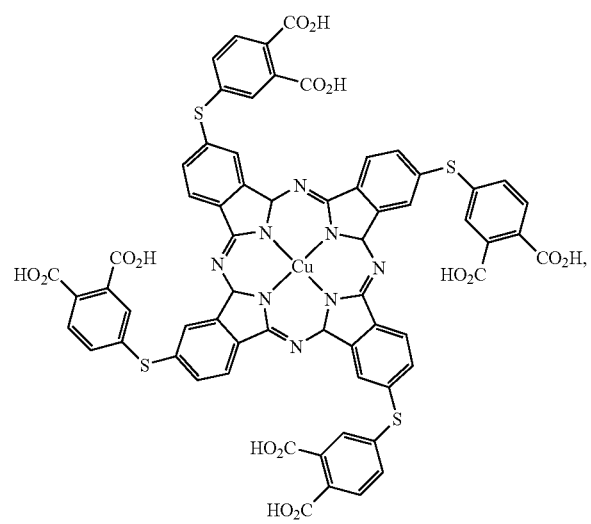
(4D)
(4E)
-continued
(4F)
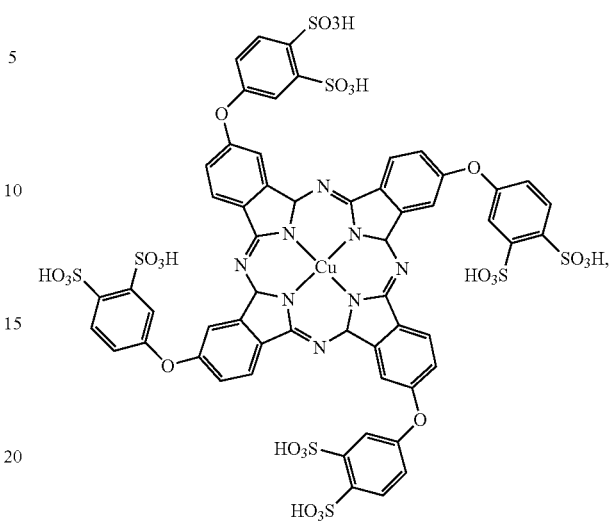
(4G)
(4H)
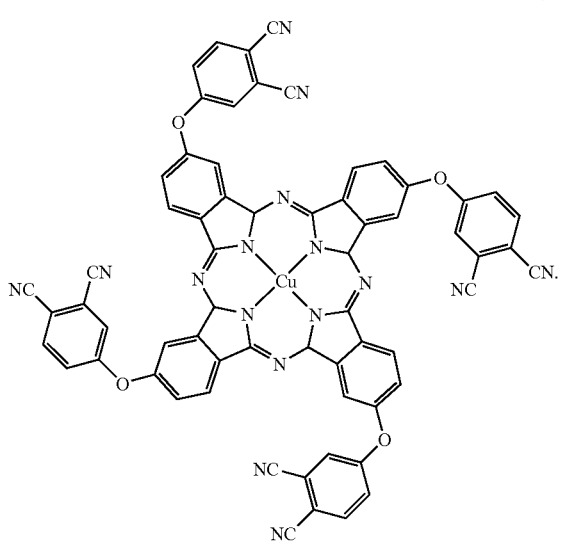

(5)
15. The organic light emitting diode of claim 10, wherein the dendritic molecule is represented by one of Formulae 5 and 6:
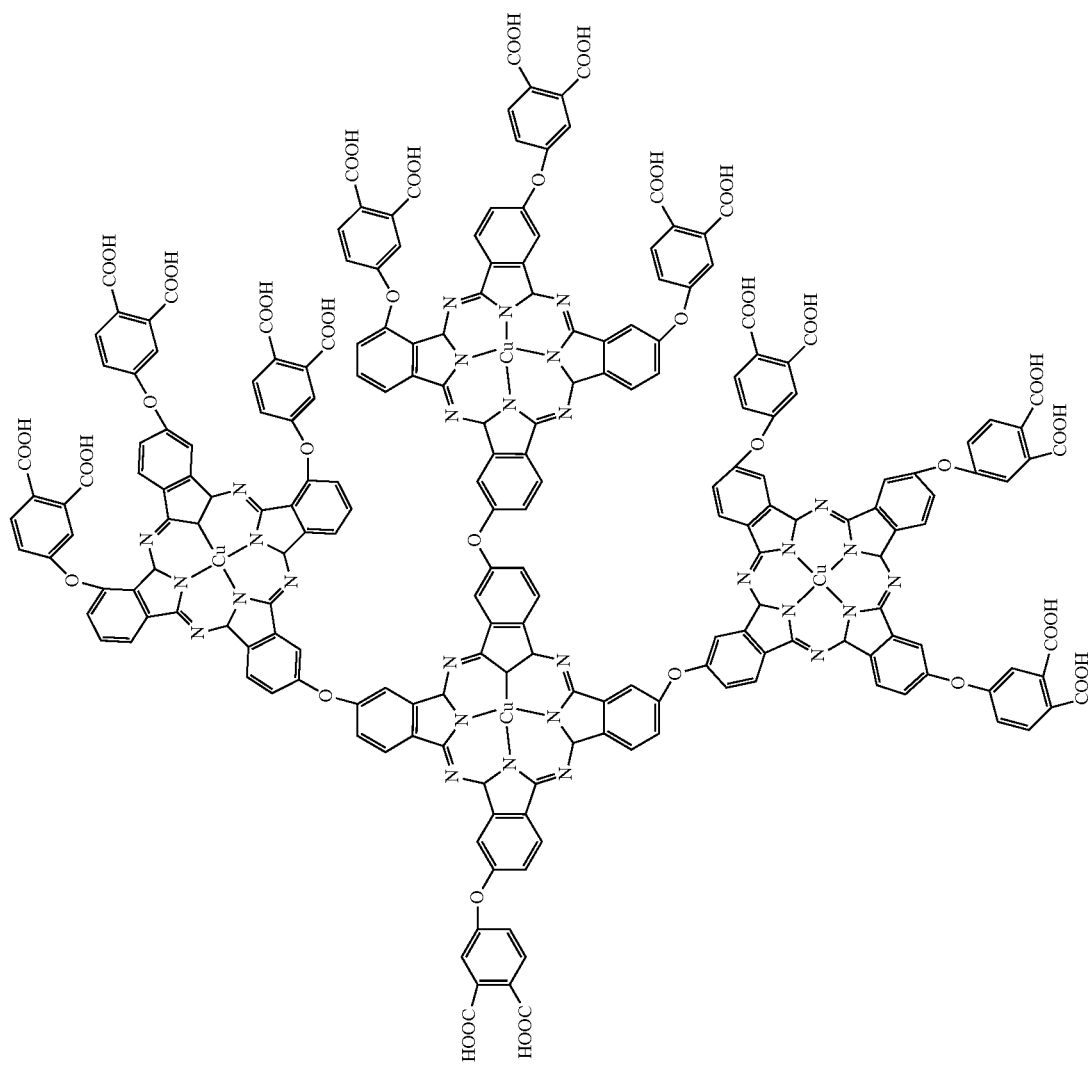

-continued
(6)
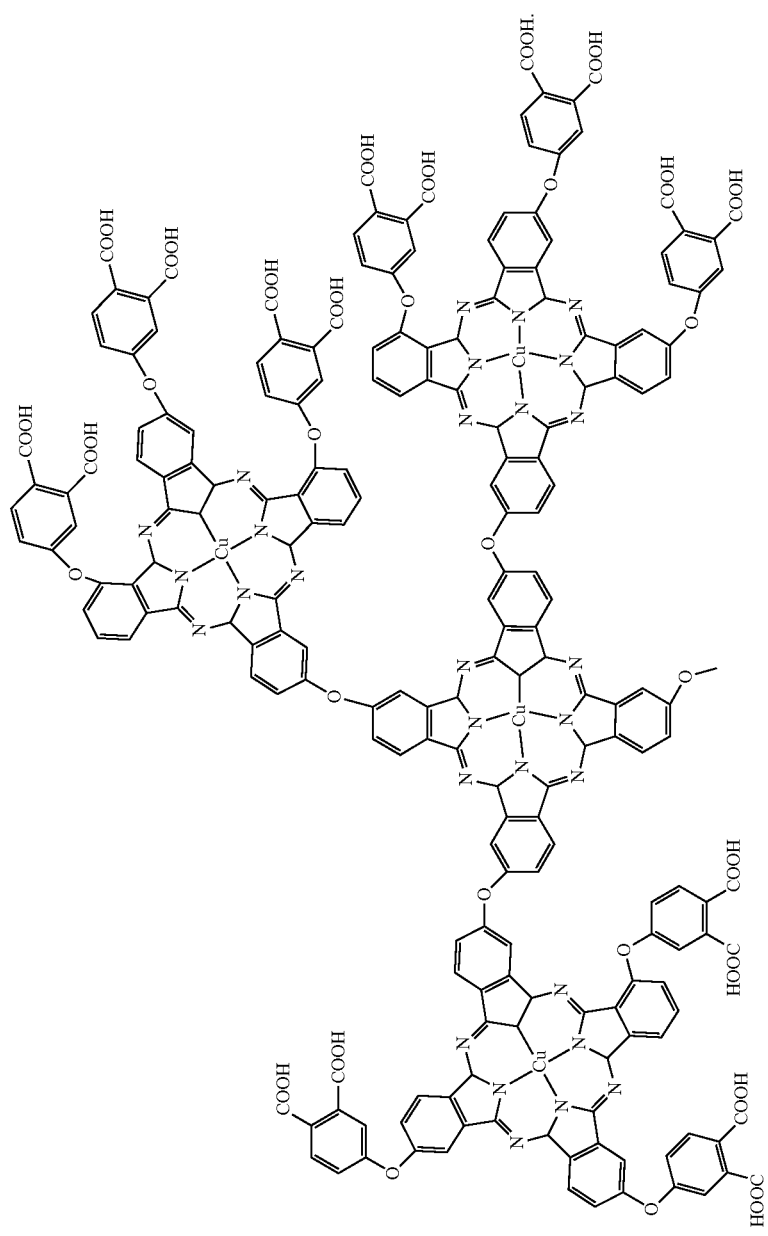

-continued
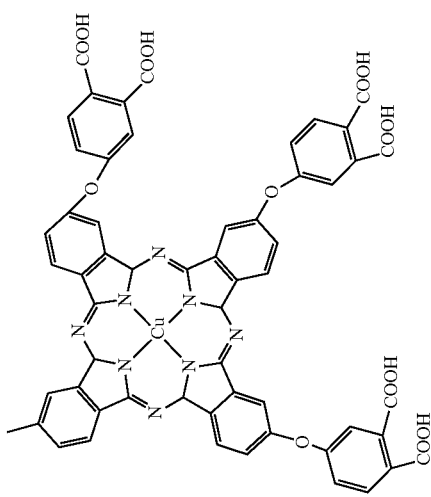

16. The organic light emitting diode of claim 10, wherein X is selected from the group consisting of S, $CH_2$, CO, $SO_2$ and NHCO.

17. The organic light emitting diode of claim 10, wherein X is selected from the group consisting of $CH_2$, CO and $SO_2$.

18. The dendritic molecule of claim 1, wherein where X is selected from the group consisting of $CH_2$ and $SO_2$.

19. A dendritic molecule represented by Formula 1:

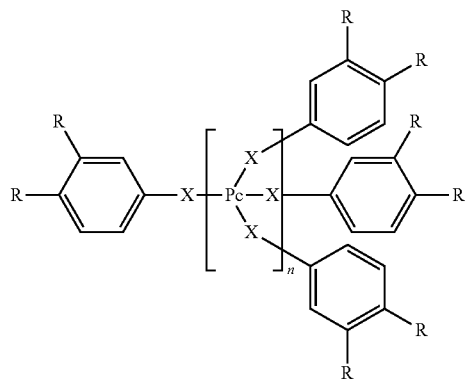

(1)

where Pc is metal phthalocyanine represented by Formula 2:

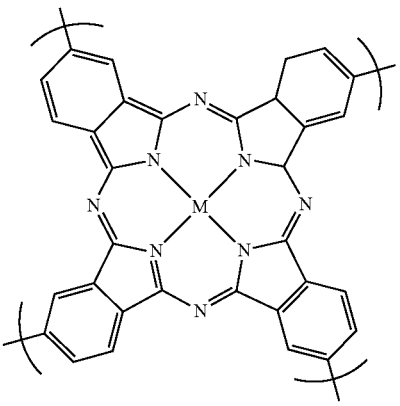

(2)

where M is a core metal of the dendritic molecule;

n is an integer in the range of 1 to 50;

each of the Xs is a bivalent linking group independently selected from the group consisting of $CH_2$, $SO_2$ and NHCO; and each of the Rs is independently selected from the group consisting of CN, COOH, $SO_3H$ and $PO_3H$.

* * * * *